(12) United States Patent
Paulson et al.

(10) Patent No.: US 12,025,583 B2
(45) Date of Patent: Jul. 2, 2024

(54) METHOD AND APPARATUS FOR ELECTROMAGNETIC TESTING OF PIPES

(71) Applicant: PURE TECHNOLOGIES LTD., Calgary (CA)

(72) Inventors: Peter O. Paulson, Calgary (CA); Jeffrey Chak-Fai Kwan, Markham (CA); Eric Nicholas Toffin, Calgary (CA)

(73) Assignee: Pure Technologies U.S. Inc., Columbia, MD (US)

( * ) Notice: Subject to any disclaimer, the term of this patent is extended or adjusted under 35 U.S.C. 154(b) by 24 days.

(21) Appl. No.: 17/258,795

(22) PCT Filed: Jul. 10, 2019

(86) PCT No.: PCT/CA2019/050949
§ 371 (c)(1),
(2) Date: Jan. 8, 2021

(87) PCT Pub. No.: WO2020/010455
PCT Pub. Date: Jan. 16, 2020

(65) Prior Publication Data
US 2021/0285914 A1    Sep. 16, 2021

Related U.S. Application Data

(60) Provisional application No. 62/696,062, filed on Jul. 10, 2018.

(51) Int. Cl.
*G01N 27/82* (2006.01)
*G01N 33/2045* (2019.01)

(52) U.S. Cl.
CPC ......... *G01N 27/82* (2013.01); *G01N 33/2045* (2019.01)

(58) Field of Classification Search
CPC ..... G01N 27/82; G01N 27/87; G01N 33/2045
See application file for complete search history.

(56) References Cited

U.S. PATENT DOCUMENTS

| 3,449,662 A | 6/1969 | Wood |
| 5,351,564 A | 10/1994 | Watson et al. |
| 5,623,203 A * | 4/1997 | Hosohara ............. G01N 27/902 324/242 |

(Continued)

FOREIGN PATENT DOCUMENTS

EP    0523880    1/1993

OTHER PUBLICATIONS

Search Report & Written Opinion issued in Int'l App. No. PCT/CA2019/050949 (2019).

*Primary Examiner* — Dominic E Hawkins
(74) *Attorney, Agent, or Firm* — Stanek Lemon Crouse & Meeks, PA

(57) ABSTRACT

Apparatus and device for testing within a metal pipe are described. The apparatus includes an exciter for generating an electromagnetic (EM) field for exciting a wall of the metal pipe; an extendable and retractable sensor assembly comprising a plurality of sensor bars arranged in an angled manner with respect to an axis of the pipe for sensing residue EM field on a wall of the pipe; a plurality of guide wheel assemblies for supporting and moving the apparatus along the axis of the pipe; and a control unit for recording sensed data from the sensor assembly.

29 Claims, 21 Drawing Sheets

(56) References Cited

U.S. PATENT DOCUMENTS

| | | | |
|---|---|---|---|
| 6,232,773 B1* | 5/2001 | Jacobs | G01N 27/82 324/242 |
| 7,154,264 B2* | 12/2006 | Burkhardt | G01N 27/902 324/238 |
| 2008/0042646 A1* | 2/2008 | Burkhardt | G01N 27/82 324/240 |
| 2008/0204008 A1* | 8/2008 | Paulson | F16L 55/46 324/220 |
| 2010/0300184 A1* | 12/2010 | Wayman | G01N 17/02 73/73 |
| 2011/0167914 A1* | 7/2011 | Sutherland | G01N 27/902 73/643 |
| 2016/0167094 A1* | 6/2016 | Danilov | B60L 7/28 15/104.061 |
| 2016/0282504 A1* | 9/2016 | Wilson | E21B 47/002 |
| 2019/0145931 A1* | 5/2019 | Feng | G01N 27/83 324/222 |
| 2019/0219473 A1* | 7/2019 | Littlestar | G01M 5/0091 |

* cited by examiner

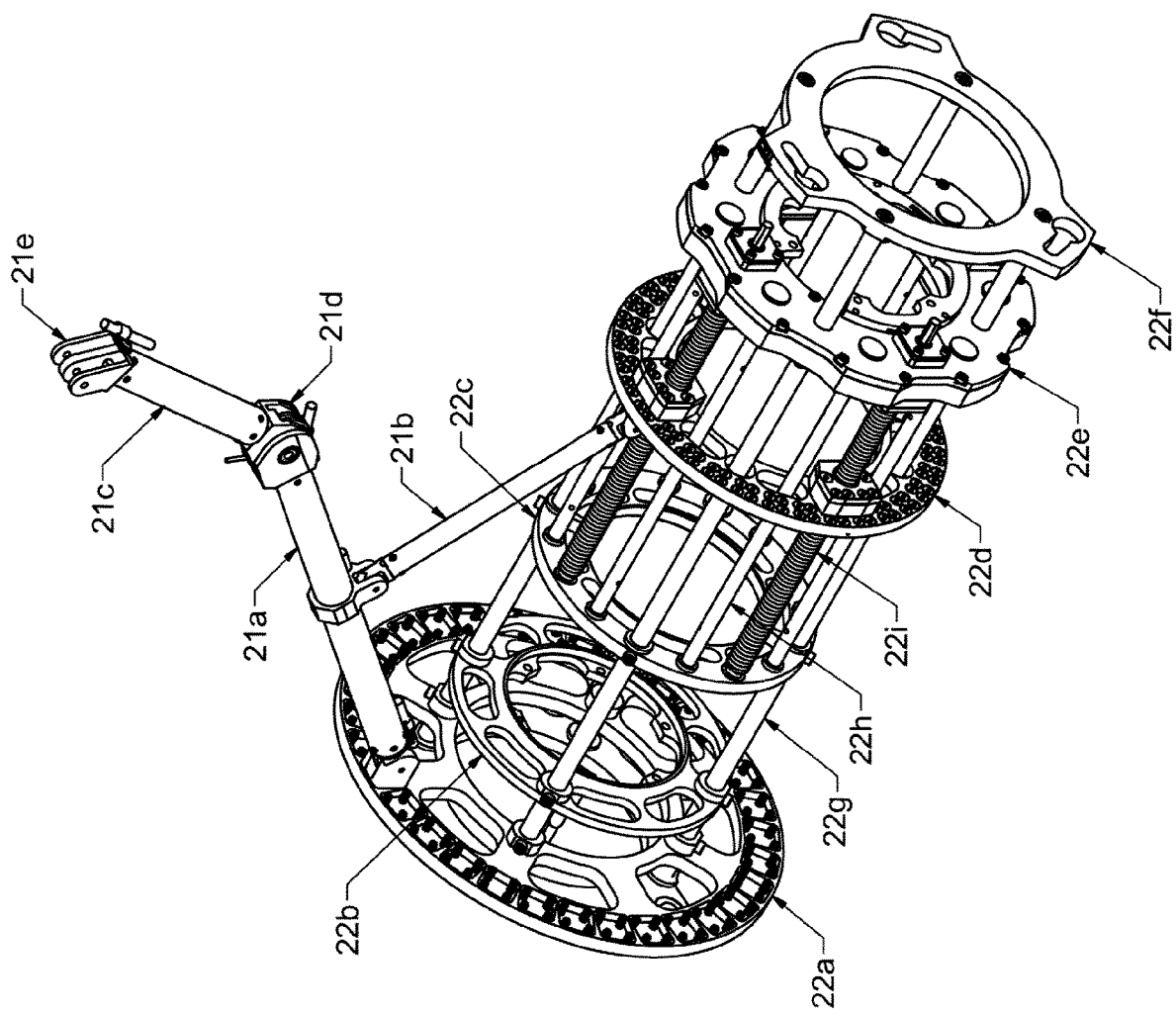

METHOD AND APPARATUS FOR ELECTROMAGNETIC TESTING OF PIPES

CROSS REFERENCE TO RELATED APPLICATIONS

This application is a U.S. nationalization under 35 USC § 371 of International Application No. PCT/CA2019/050949, filed 10 Jul. 2019, which claims the benefit of U.S. Provisional Application Ser. No. 62/696,062, filed 10 Jul. 2018. The disclosures set forth in the referenced applications are incorporated herein by reference in their entireties.

FIELD

The present application generally relates to pipe testing, in particular to method and apparatus for electromagnetic testing of a pipe.

BACKGROUND

Metallic pipes make up a majority of large diameter pipelines in many parts of the world. In some pipelines, such as oil and gas pipelines, inspection is usually done by pumping an inspection tool through the length of the pipeline. This type of inspection is enabled in oil and gas pipelines by the provision of specialized launching and receiving stations constructed into the pipeline.

For water and wastewater pipelines, no such launching and receiving apparatus is usually available. In order to perform in-line inspection, tools must be designed that can enter the pipeline through manway inspection flanges, yet still be capable of inspecting the entire inner circumference of the pipe.

In pipeline pigging technology, some tools can allow modest diameter changes by allowing groups of sensors to compress or expand, such as an Magnetic Flux Leakage (MFL) tool produced by Rosen and others.

All of these arrangements are suitable for pigging equipment where weight and size of the tools for entry into the pipeline are not factors in the design. Pigging refers to the practice of using devices known as "pigs" to perform various maintenance operations of pipeline, including cleaning and inspecting the pipeline, without stopping the flow of the product in the pipeline. This is accomplished by inserting the pig into a "pig launcher" (or "launching station")—an oversized section in the pipeline, reducing to the normal diameter. The launching station is then closed and the pressure-driven flow of the product in the pipeline is used to push the pig along down the pipe until it reaches the receiving trap—the "pig catcher" (or "receiving station").

However, the arrangements of pipeline pigging technology are unsuitable for the insertion through manholes due to the size of the tools, for large changes in pipeline size, and for maintaining a modest mass.

BRIEF DESCRIPTION OF THE DRAWINGS

Reference will now be made, by way of example, to the accompanying drawings which show example embodiments of the present application, and in which:

FIG. 3 is a perspective view of an expandable structure of the sensor assembly in FIG. 2, according to an embodiment of the present disclosure;

Similar reference numerals may have been used in different figures to denote similar components.

SUMMARY OF THE INVENTION

The apparatus of the present application mitigates space and sensor count limitation of the existing tools by using collapsible packaging design, while still allowing the apparatus to pass through a manhole entry point.

As well, the apparatus of the present application is designed to substantially reduce the mass of the apparatus to allow manual or powered movement through a pipe.

The apparatus of the present application provides a large number of sensors, but does not require intervention to add or remove sensors when the pipe diameter changes, or when the pipe becomes oval. For example, sometimes the pipe transitions to oval from circular.

The present invention utilizes a series of sensors deployed in a way that adjacent sensors are configured to be overlapped to allow a nesting, or an angled arrangement of sensor bars or pods. The angled arrangement provides that a minimum sensor density is maintained through large diameter changes in the pipe being tested. The overlapping sensor tracks simply provide more or less duplicate data where overlap occurs, but expands as needed to provide less overlap as the pipe diameter increases. As the sensor bars are moved along the axis of the pipeline, each point on the pipeline wall has at least one sensor passing nearby. In other words, each point of the inner circumference of the pipeline is sensed by at least one sensor of the apparatus notwithstanding substantial changes in diameters of the pipe.

In an embodiment, there is provided an apparatus, which includes an exciter for generating an electromagnetic (EM) field; an extendable and retractable sensor assembly comprising a plurality of sensor bars arranged in an angled manner with respect to an axis of the pipe for sensing the EM field on a wall of the pipe, each sensor bar comprising a plurality of sensors; a plurality of guide wheel assemblies for supporting and moving the apparatus along the axis of the pipe; and a control unit for recording sensed data from the sensor assembly.

DESCRIPTION OF EXAMPLE EMBODIMENTS

Figure 1:
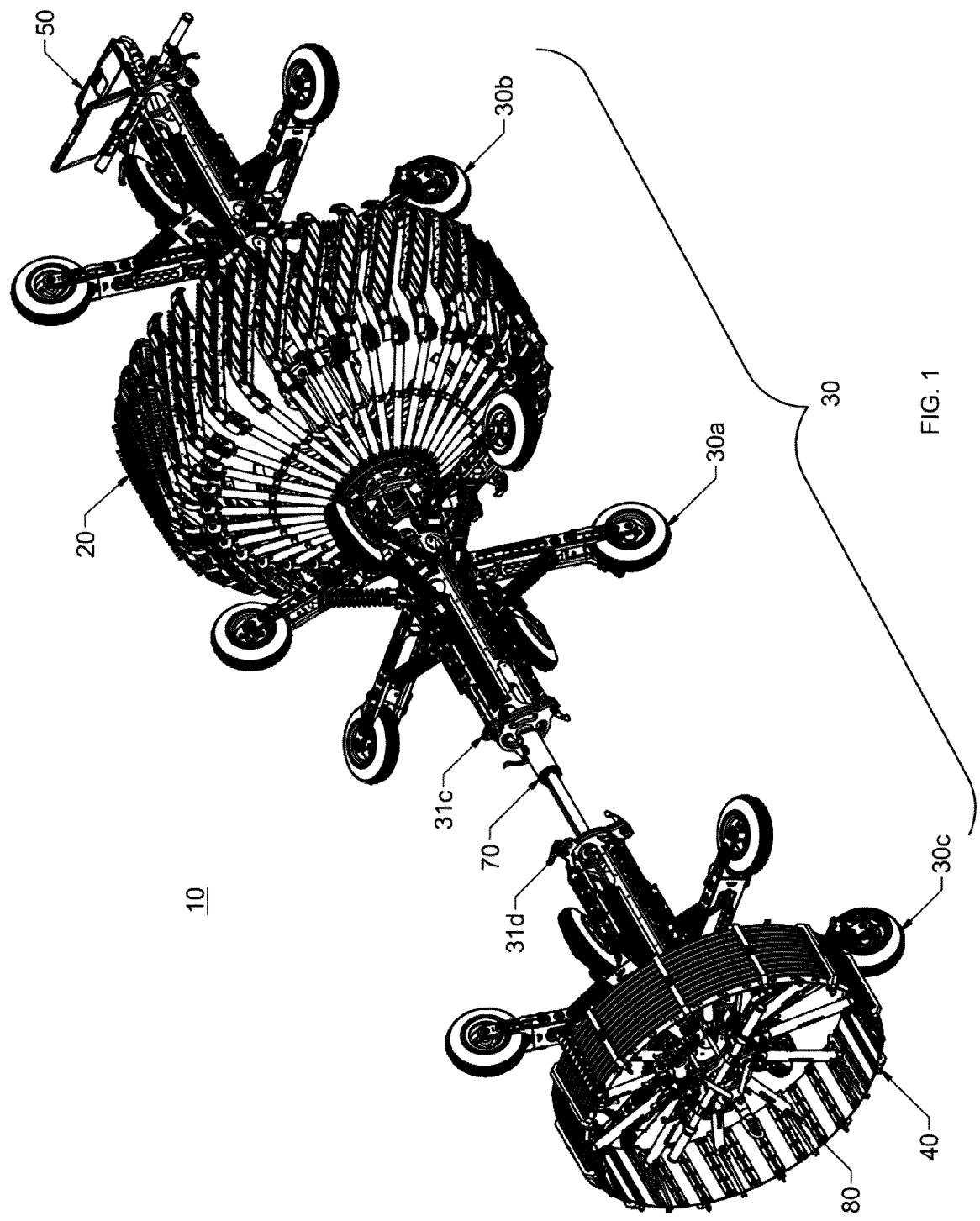
FIG. 1 is a perspective view of an apparatus, according to an embodiment of the present disclosure.

FIG. 1 illustrates an exemplary apparatus 10 for electromagnetic (EM) testing of pipes. The apparatus 10 may be inserted into a pipeline, for example via a manhole, for moving inside the pipeline along the axis of the pipeline to detect defects of the pipeline. The apparatus 10 may include a sensor assembly 20 for sensing the EM field on the wall of the pipes, a plurality of guide wheel assemblies 30 for supporting and moving the apparatus 10 along the axis of a pipeline, an exciter 40 for generating EM field to induce electric currents or magnetic fields or EM fields inside the metal wall of a pipeline, and a control unit 50 for controlling generation of EM field and recording testing results.

In the example of FIG. 1, the sensor assembly 20 is connected with a first wheel guide assembly 30a at one end of the sensor assembly 20 and a second wheel guide assembly 30b at the other end of the sensor assembly 20. Both the wheel guide assemblies 30a and 30b may support the sensor assembly 20 and guide the movement of the sensor assembly 20. An end of the wheel guide assembly 30c is connected with wheel guide assembly 30a. The exciter 40 is connected to the other end of the wheel guide assembly 30c. The guide wheel assembly 30c may support the exciter 40 and guide the movement of the exciter 40. The control unit 50 is electrically connected with the sensor assembly 20 for receiving the sensed signals or data from the sensors placed in the sensor assembly 20. The control unit 50 is also electrically connected with the exciter 40 for providing modulated current to the exciter 40 in order to generate EM field. More or fewer guide wheel assemblies 30 may be used at different positions of the apparatus 10 to provide stability to the apparatus 10 and to move the apparatus 10 along the axis or the central line of a pipe.

Figure 2:
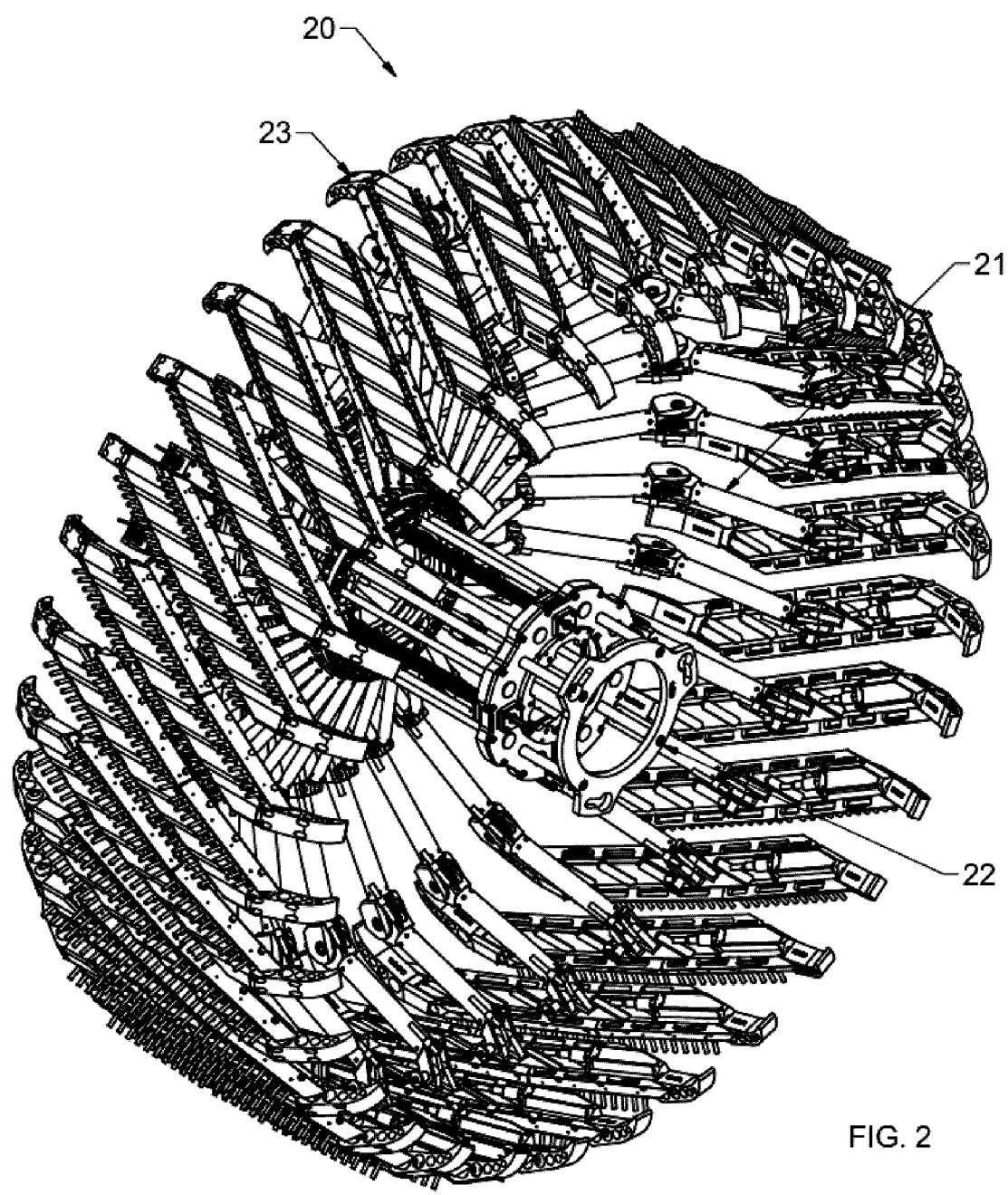
FIG. 2 is a perspective view of a sensor assembly of the apparatus in FIG. 1, according to an embodiment of the present disclosure.

References are made to FIGS. 2-8. As illustrated in FIG. 2, the sensor assembly 20 includes a plurality of sensor bars 23 placed on a plurality of expandable arms 21, and a support structure 22 for supporting the expandable arms 21 and the sensors bars 23. Each arm 21 has a sensor bar 23 that includes a plurality of the sensors for measuring the magnetic flux of the wall of the pipeline induced by the EM fields generated by the exciter 40. The sensor bars 23 are arranged in an angled manner in relation to the axis of the pipeline, so that each point on the inner wall of a pipe is sensed by at least one sensor, notwithstanding substantial changes in diameters of the pipe. The arms 21 and sensor bars 23 are configured to be urged against the inner wall of the pipe, or folded against the body of the apparatus 10, for example, for passage through the manway.

The sensor assembly 20 may expand or retract based on the dimension of the pipe, or based on the change of diameters of the pipe, to an extent that that the sensors of the sensor assembly 20 and the inner wall of the pipeline are within a range that the sensors can detect the magnetic flux from the wall of the pipeline. In some examples, the arms 21 are configured to urge the sensor bars 23 outward until the sensor bars 23 contact with the inner wall of the pipe.

Figure 2A:
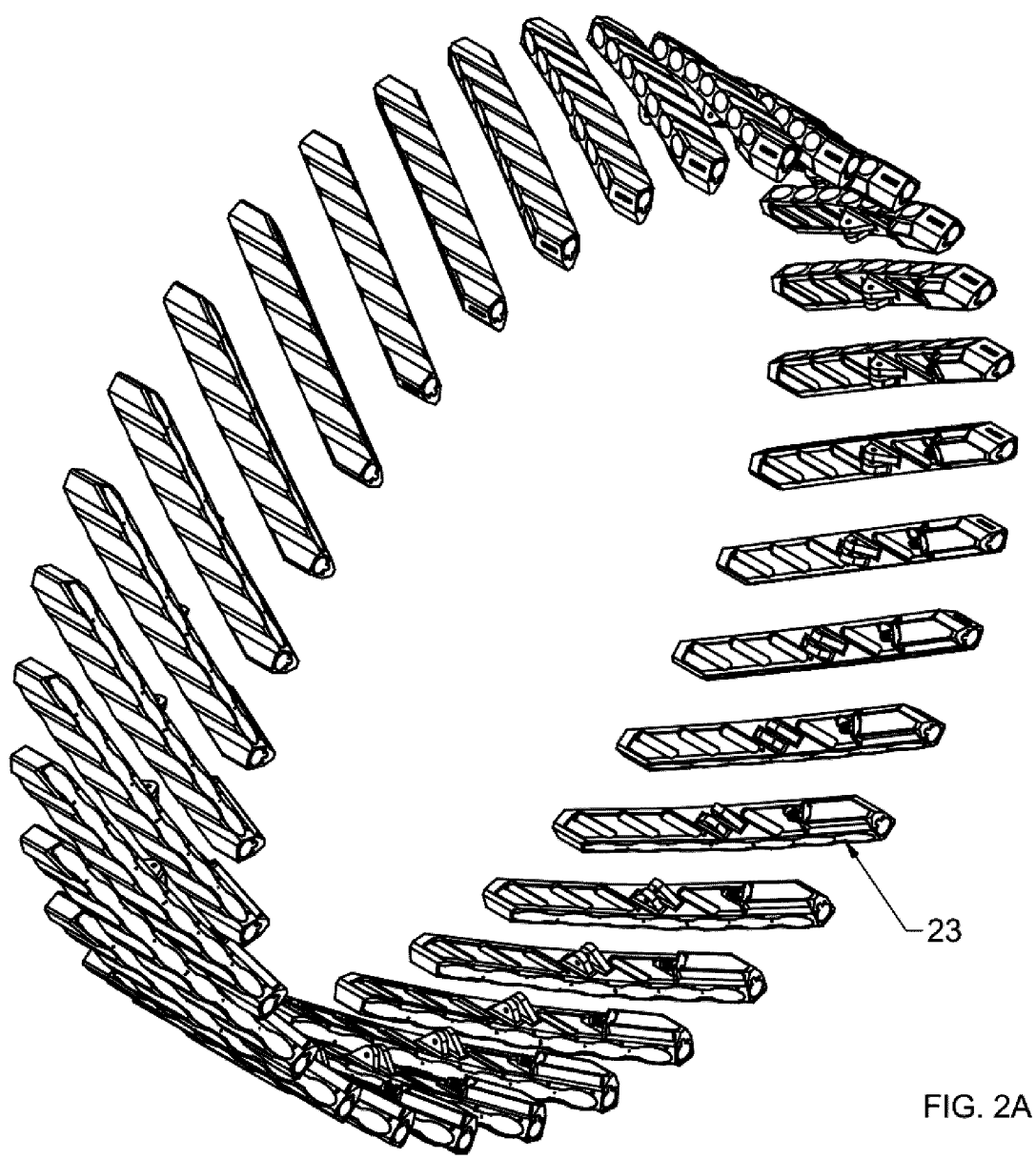
FIG. 2A is a perspective view of an arrangement of sensor bars of the sensor assembly in FIG. 1, according to an embodiment of the present disclosure.

In the example shown in FIGS. 2 and 2A, the arrangement of the arms 21, each with a sensor bar 23 mounted on the support structure 22, to form a circumference when the sensor assembly 20 expands inside the pipe, provides stability of the apparatus 10 in the movement of the apparatus 10. This in turn improves the reliability of the sensed signals or data.

In the example of FIG. 3, each arm 21 is installed on the support structure 22. The support structure 22 includes a plurality of the flanges 22a, 22b, 22c, 22d and 22f, and a plurality of rods 22g and 22h. The rods 22g are longer than the rods 22h. The flange 22c and gearbox 22e are secured on the rods 22h through the holes on the flanges 22c and gearbox 22e. Flange 22d is slidably connected to the rods 22h through the holes on the flange 22d. The flanges 22a, 22b, 22c, and 22f are secured to the rods 22g through the holes on each of the flanges 22a 22b, 22c, and 22f, and the gear box 22e. Flange 22d is slidably connected to the rods 22g through the holes on the flange 22d. Gearbox 22e can be turned with a socket wrench manually. The gearbox 22e may push or pull the flange 22d by driving one or more lead screws 22i. Pushing and pulling the flange 22d, which is linked to arm 21b, expands and retracts all the arms 21 together.

As illustrated in FIG. 3, each arm 21 includes a first segment 21a, a second segment 21b, and a third segment 21c. The first segment 21a has a first end pivotally installed on the flange disc 22a at joint 21f and a second end pivotally joined the first end of the third segment 21c at the joint 21d. The joint 21d may include a spring to press the third segment 21c away from the first segment 21a. The first end of the second segment 21b is pivotally attached to the first segment 21a, for example, by pivotally connecting with a sleeve surrounding the first segment 21a. The second end of the second segment 21b is pivotally attached to the flange disc 22d. Pushing and pulling the flange 22d respectively expands and retracts arm 21b which cause the arm 21a to respectively expand and retracts. The second end of the third segment 21c is configured to pivotally receive a sensor bar 23 at the pivotal joint 21e, so that the sensor bar 23 is substantially parallel to the surface of the inner wall of a pipeline when the apparatus 10 moves along a pipe.

In an example, the sensor assembly 20 is expanded to the pipe diameter manually through the gearbox 22e by driving the 4 lead screws 22i. The spring in joint 21d may further drive the sensor bars 23 towards the pipe wall to compensate for pipe diameter or ovality change. For examples, the spring in joint 21d may compensate for a 10% pipe diameter or ovality change. In some examples, In some examples, the wall of the pipeline pushes the sensor bar 23 downwardly when the diameter of the pipeline becomes smaller, or the spring in the joint 21d pushes the sensor bar 23 upwardly when the diameter of the pipeline becomes larger. When the diameter of the pipe becomes smaller, the downward movement of the sensor bar 23 urges the relative downward movement of the segment 21c. When moving in the pipe in pipe testing, the position of the first segment 21a may remain unchanged. If there is a substantial change in pipe diameter, the gearbox 22e may be further adjusted to make the sensor bars 23 in close proximity of wall of the pipe.

Figure 4:
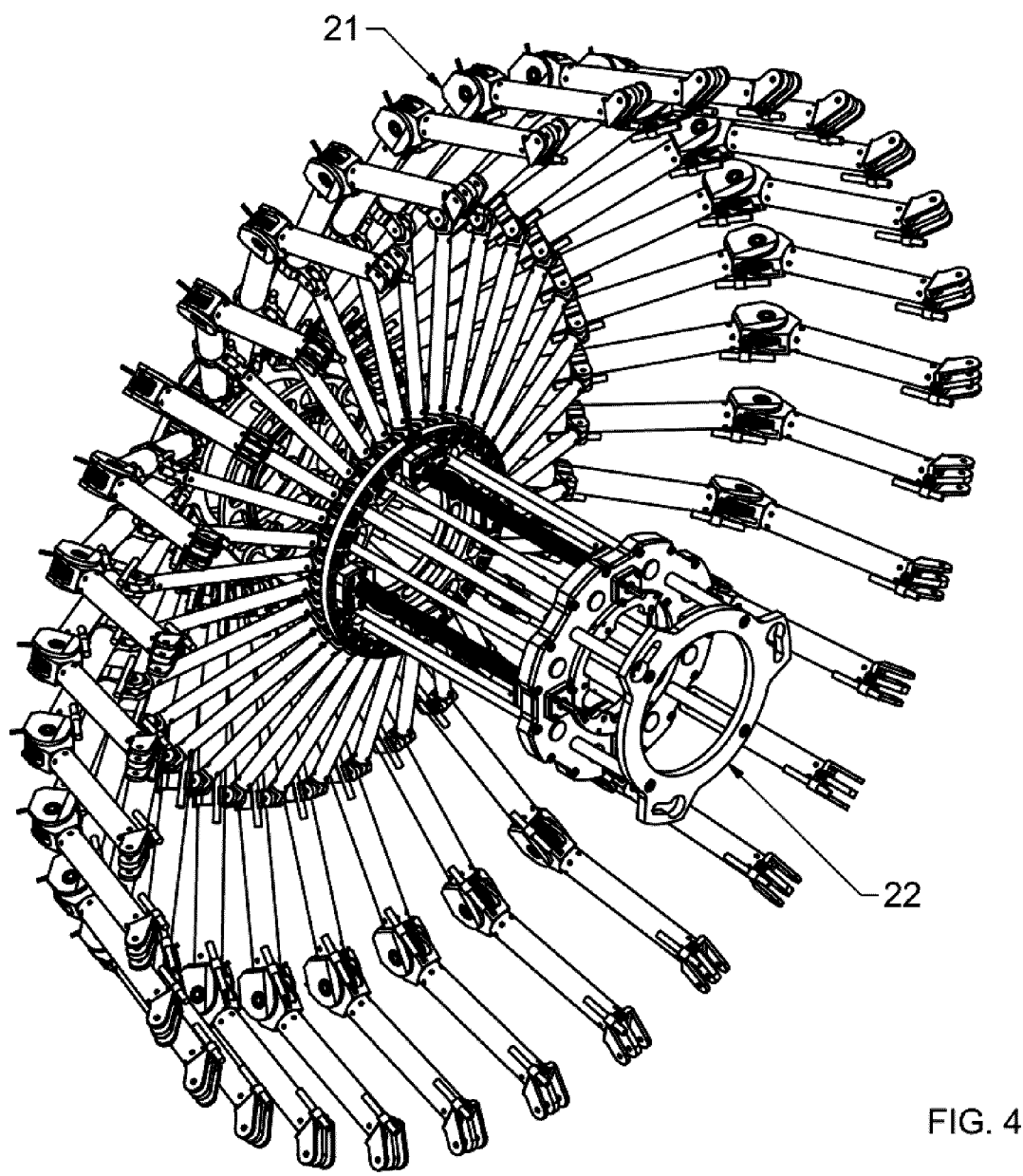
FIG. 4 is a perspective view of the structure of FIG. 3 in an expanded configuration.
Figure 5:
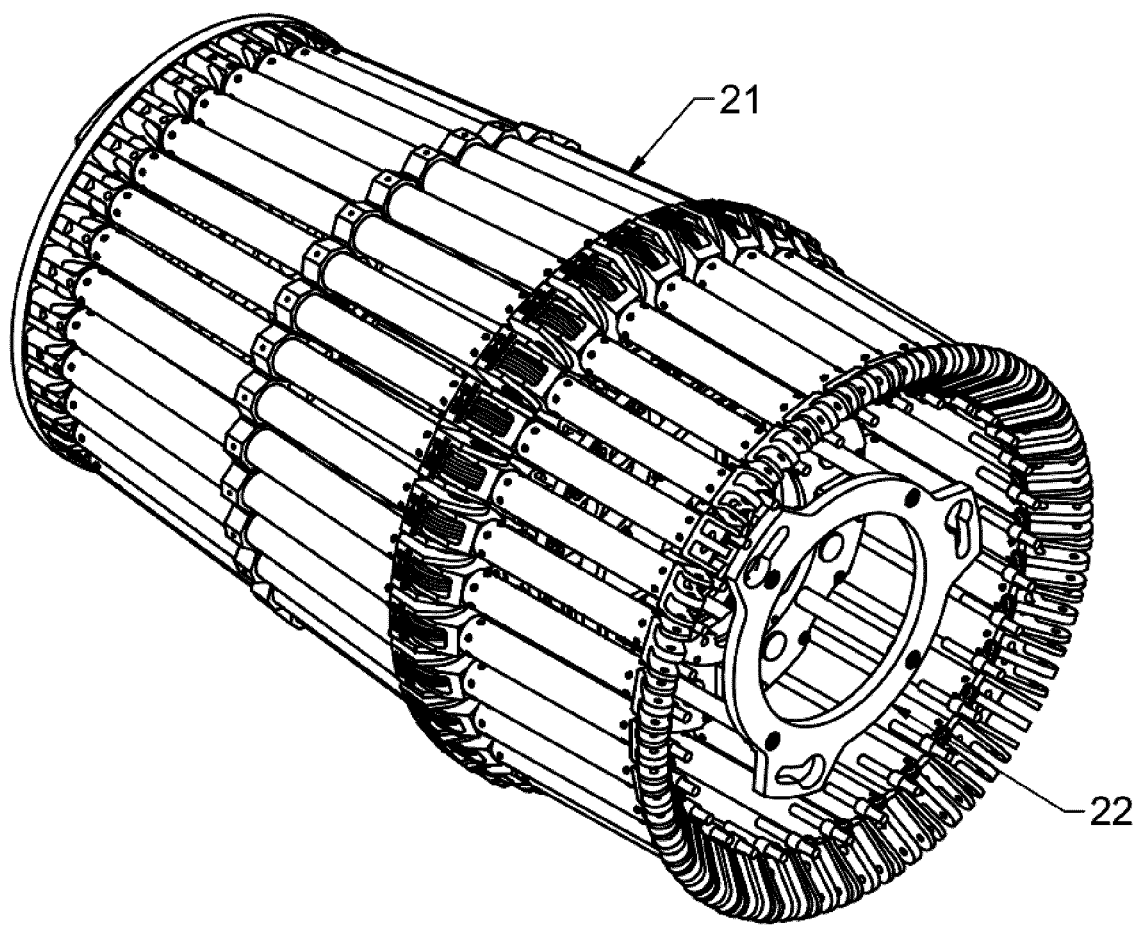
FIG. 5 is a perspective view of the structure of FIG. 4 in a retracted configuration.

FIG. 4 illustrates an example that the arms 21 are fully extended away from the support structure 22. In this state, the flange 22d is substantially adjacent to the flange 22c. FIG. 5 illustrates an example that the arms 21 are fully retracted and close to the support structure 22, for example, when the apparatus passes through a manway. In this state, the flange 22d is substantially adjacent to the gearbox 22e.

Figure 6A:
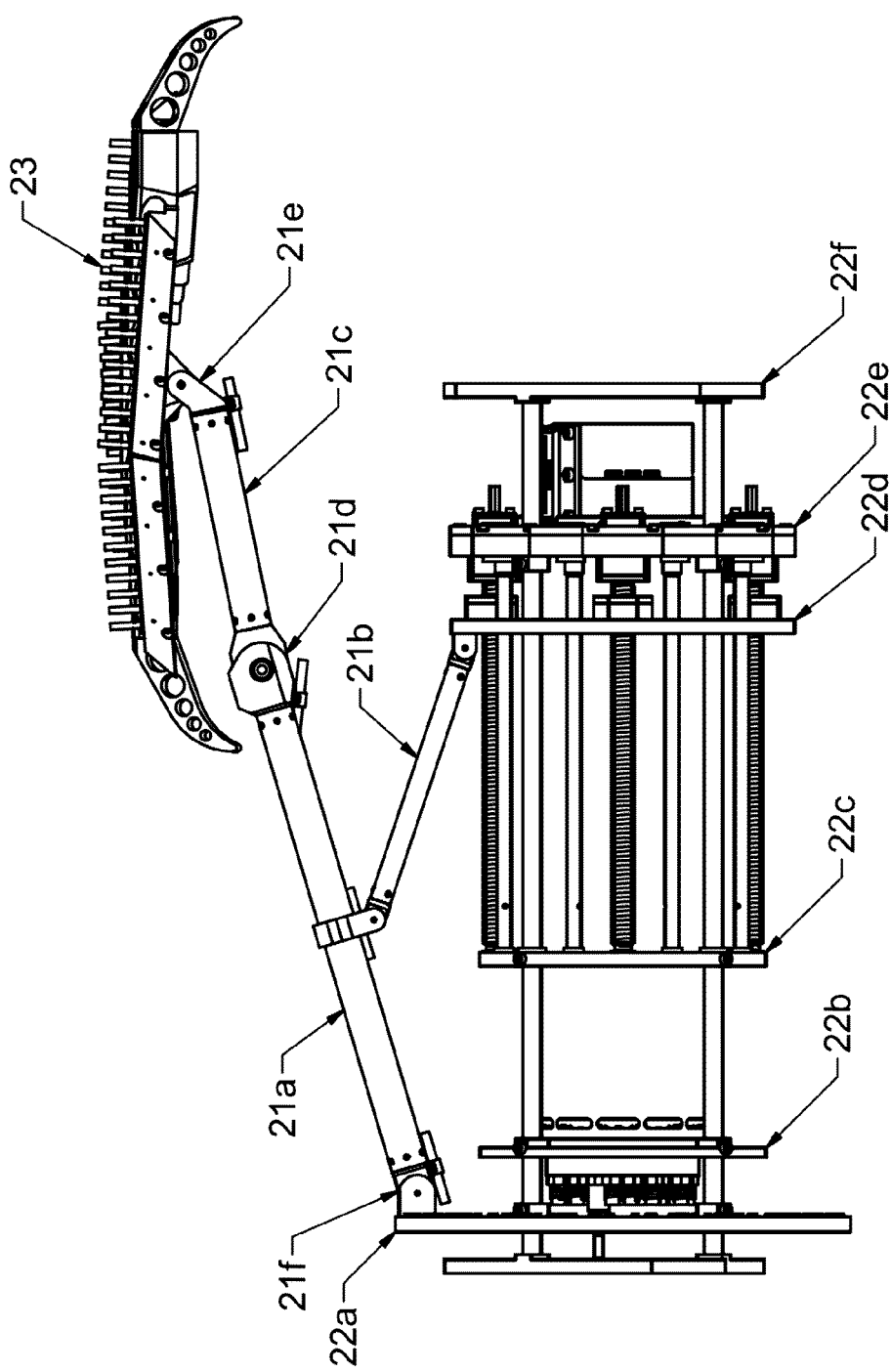
FIGS. 6a, 6b, and 6c are perspective views of an arm of the expandable structure of the sensor assembly in FIG. 2 in a first position, a second position, and a third position, respectively.
Figure 6B:
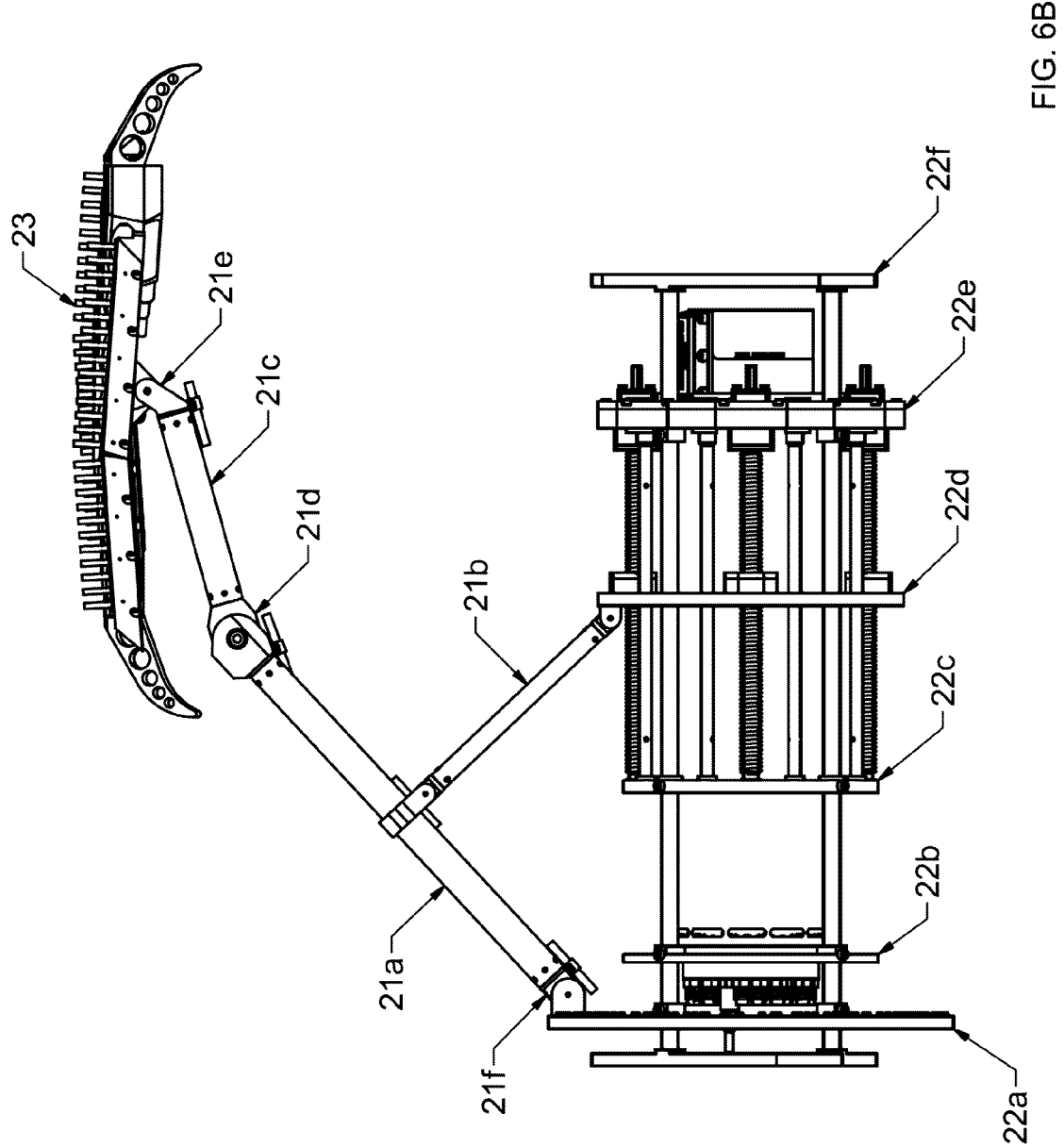
Figure 6C:
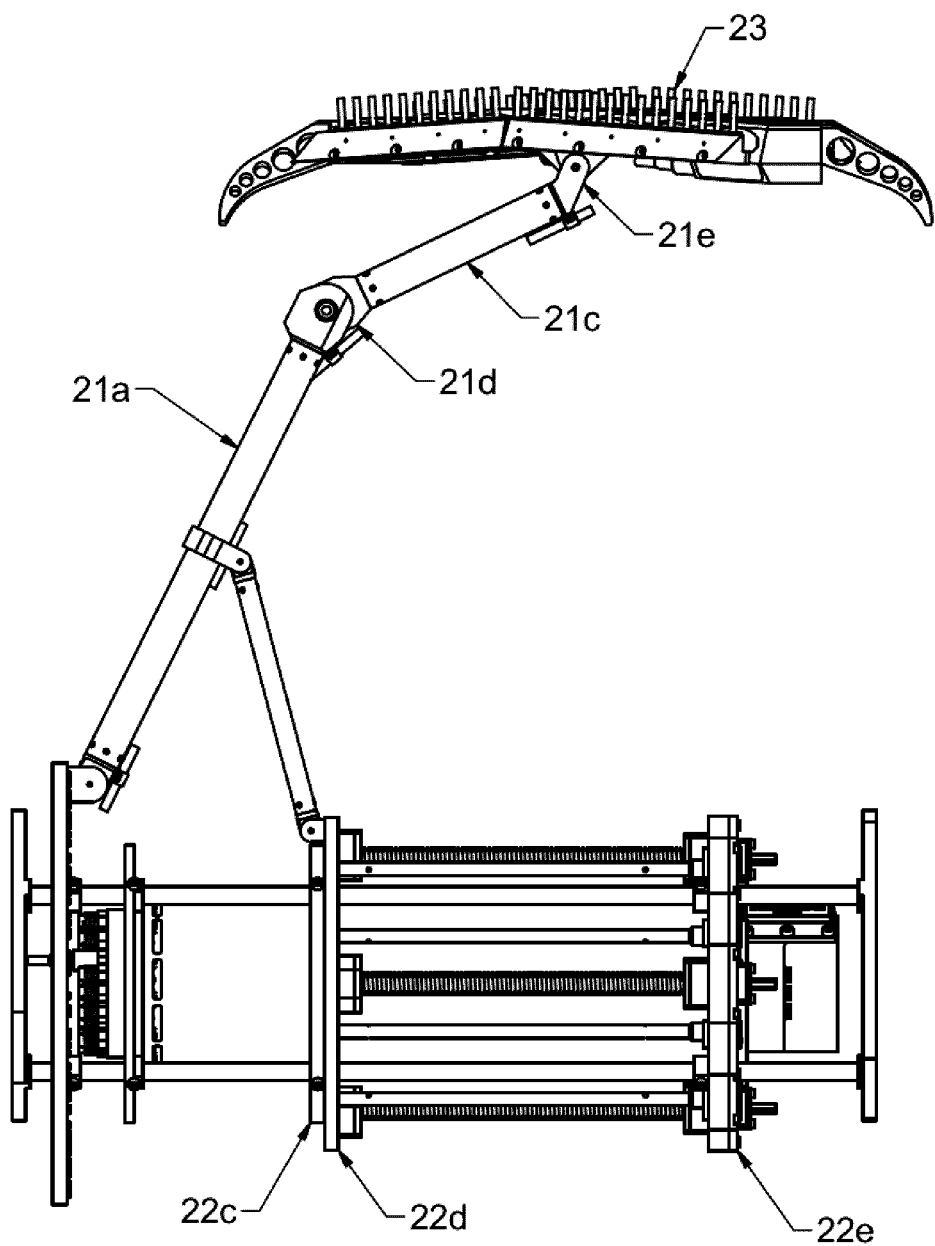

Examples of FIGS. 6A-6C illustrate different positions of the arm 21 with the sensor bar 23 pivotally installed on the joint 21e. In the example of FIG. 6A, the arm 21 is substantially retracted and close to the support structure 22. The diameter of the circumference of the sensor assembly 20 (see FIG. 2A) formed by the sensing bars 23 is substantially the minimum diameter of a pipe that the apparatus 10 is configured to measure, for example, 36 inches. In the example of FIG. 6B, the arm 21 extends at a positon between the full extension and full retraction, and the diameter of the circumference of the sensor assembly 20 formed by the sensing bars 23 is between the minimum diameter and the maximum diameter of the pipe that the apparatus 10 is configured to measure. In the example of FIG. 6C, the arm 21 is substantially fully extended from the support structure 22. The diameter of the circumference of the sensor assembly 20 (see FIG. 2A) formed by the sensing bars 23 is substantially the maximum diameter of a pipeline that the apparatus 10 is configured to measure, for example, 60 inches. In the example of FIG. 6B, the arms 21 may also be extended to a position between the fully extension in the example of FIG. 6C and full retraction in the example of FIG. 6A. In some examples, the length of the arms 21 may be from 0.4 meter to 1.5 meters.

Figure 7A:
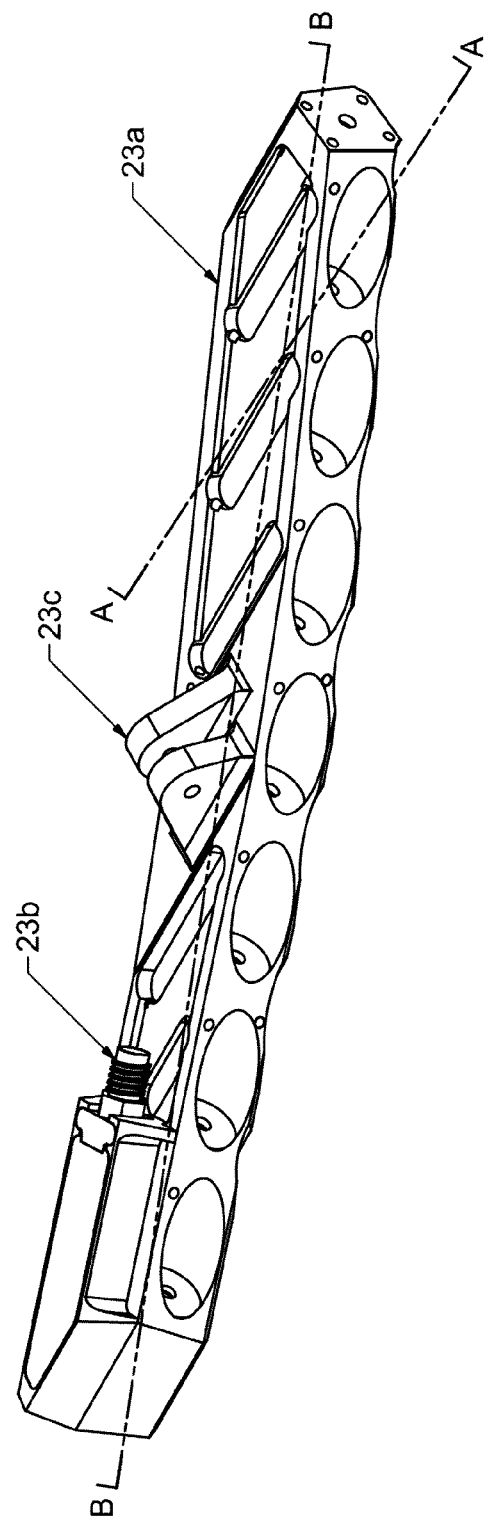
FIG. 7A is a perspective view of a sensor bar, according to an embodiment of the present disclosure.
Figure 7B:
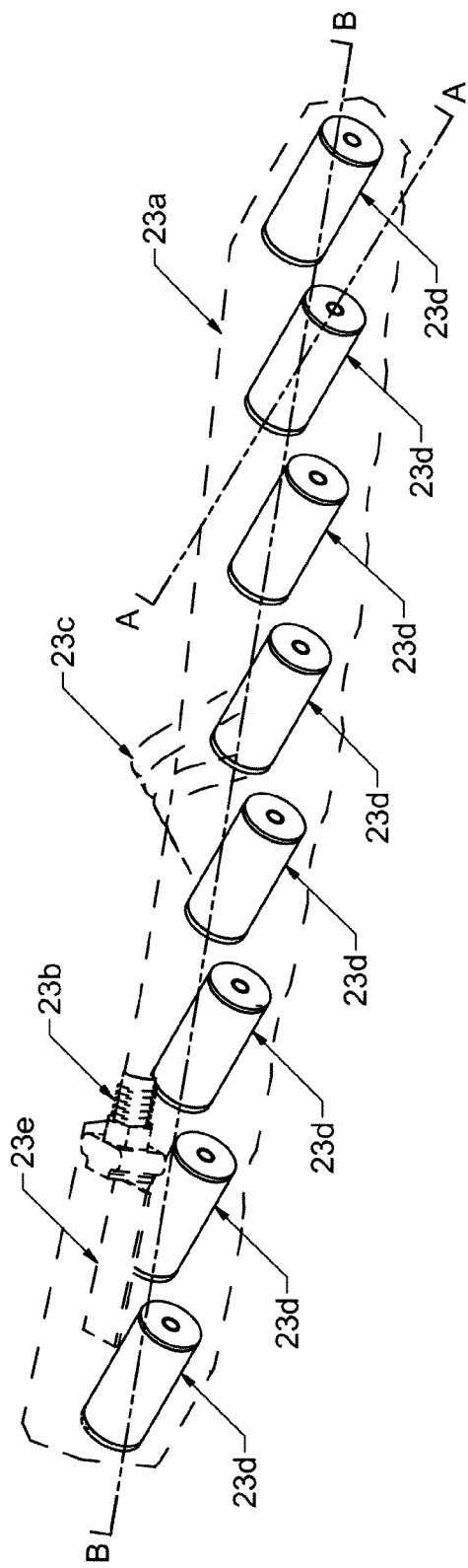
FIG. 7B is a perspective view of a plurality of sensors installed in the sensor bar of FIG. 7A.

In the example of FIGS. 7A and 7B, the sensor bar 23 includes a housing 23a, a signal output circuit 23b, a plurality of sensors 23d in the housing for detecting an EM field on the metal pipe wall. The housing 23a receives a plurality of sensors 23d inside the housing 23a. In some examples, the sensors 23d are coils. The housing 23a may be made by rubber or plastic. The signal output circuit 23b includes a circuit 23e for receiving sensed signals or data from each of the sensors 23d and an output port for transmitting the sensed signals to the control unit 50. Each sensor 23b outputs its measured signals or data to the control unit 50 via the output circuit 23b. In some examples, the housing 23a includes two protrusions 23c substantially in the mid portion of the housing 23a. The two protrusions 23c are configured to pivotally engage, for example via a pin between the two protrusions 23c, the distal end of the third segment 21c at the pivotal joint 21e for mounting a sensor bar 23 on the arm 21.

In FIGS. 7A and 7B, the sensors 23d are placed in a sensor bar 23 in such as a manner that the axis AA of the sensor 23d forms an angle with the axis BB of the sensor bar 23. The range of the angle may be from about 20°-70°. In some examples, the axis BB of the sensor bar 23 are arranged in an angled manner with the axis of the pipe, such as shown in FIGS. 2 and 2A. With one or more of these arrangements, the number of sensor bars 23 and thus the sensors 23d that can be fitted around the circumference of a pipe is increased significantly. In some examples, the sensor bar 23 may include 8 sensors 23d. As the apparatus 10 senses the pipe wall by measuring the residue electromagnetic (EM) field on the pipe wall, the resolution of the apparatus 10 is determined partly by the number of sensors 23d deployed around the circumference inside the pipe. Accordingly, increased number of sensors 23d increase the sensing resolution of the apparatus 10

The angled arrangements described above also allow the sensor bars 23 to retract or nest together as the diameter of the pipe decreases, or to separate from each other as the pipe diameter increases. As such, the sensor assembly 20 and the apparatus 10 are capable of measuring pipes with different diameters without changing the number of sensors 23d of the sensor assemble 20. By the arrangements of the collapsible arms 21 and the angled arrangements of the sensor bars 23 and the sensors 23d, a large number of sensors 23d may be used in the sensor assembly 20 to provide sufficient sensing resolution in a range of pipe diameters. Sufficient sensing resolution may refer to the residue EM field of each area of a wall of the pipe is adequately received by at least one sensor 23d. In some examples, when sufficient sensing resolution is provided, the sensors 23d fully cover the inner wall of the pipe or overlap on the inner wall of the pipe. The angled arrangement of the sensor bars 23 and the sensors 23d allows the sensor assembly 20 provides sufficient sensing resolution.

Figure 8:
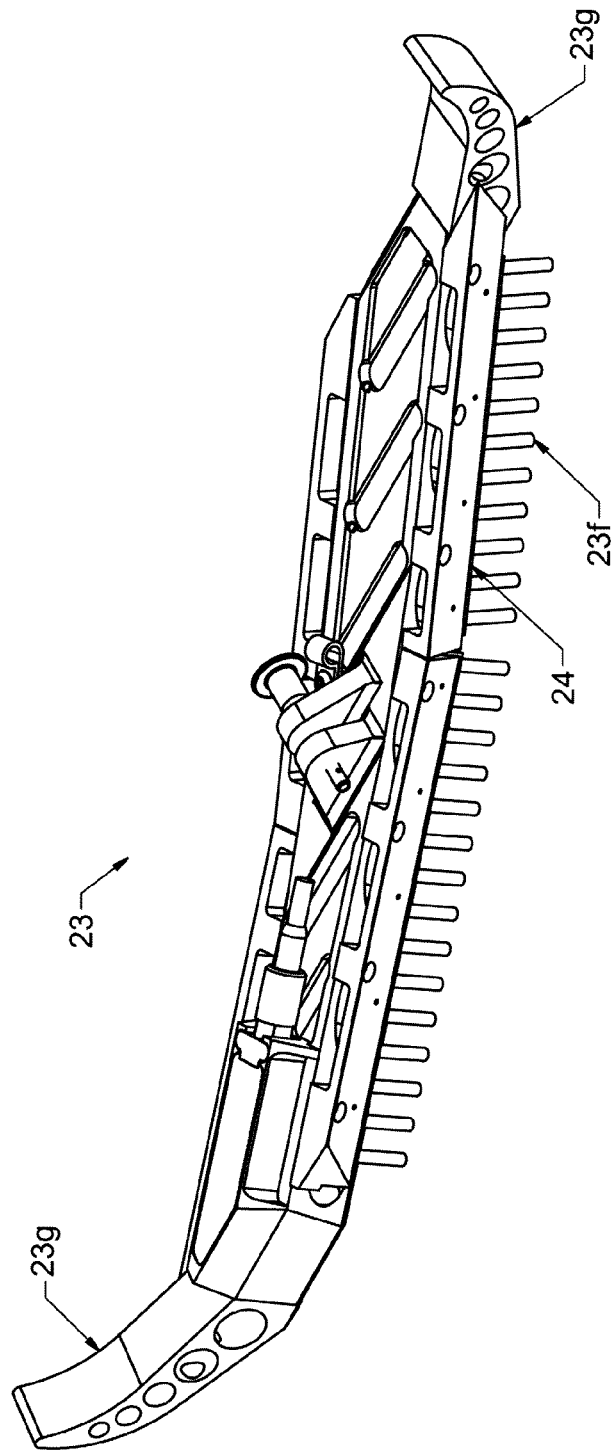
FIG. 8 is a perspective view of a sensor bar of FIG. 7A with bristles.

In some examples, as illustrated in FIG. 8, the sensor bar 23 may include bristles 23f on at least one side or end of a sensor bar 23. The bristles 23f may be used to reduce vibration of the sensor bar 23 caused by the inconsistency of the pipe wall. The bristles may be soft or stiff. Reduction of vibration on the sensor bar 23 in turn reduces vibration of the sensor 23d. As such, the measured signals more accurately reflect the condition of the pipe wall and improve the sensing results. The bristles 23f may be made of plastic and may be mounted on side bars 24 so that the bristles 23f contact with the wall of the pipeline when the apparatus 10 is in use. The side bars 24 may be mounted on at least one side of the sensor bar 23 for protecting the sensor bar 23 from scratch of the wall of the pipe. For example, the side bars 24 may be a ramp to allow the sensor bars 23 to ride over debris or tuberculation in the pipe. Each side bar 24 may be removed and replaced as needed. Each end of the sensor bar 23 may include a ski 23g to allow the sensor bar 23 to ride over debris or tuberculation in the wall of the pipe.

Figure 9:
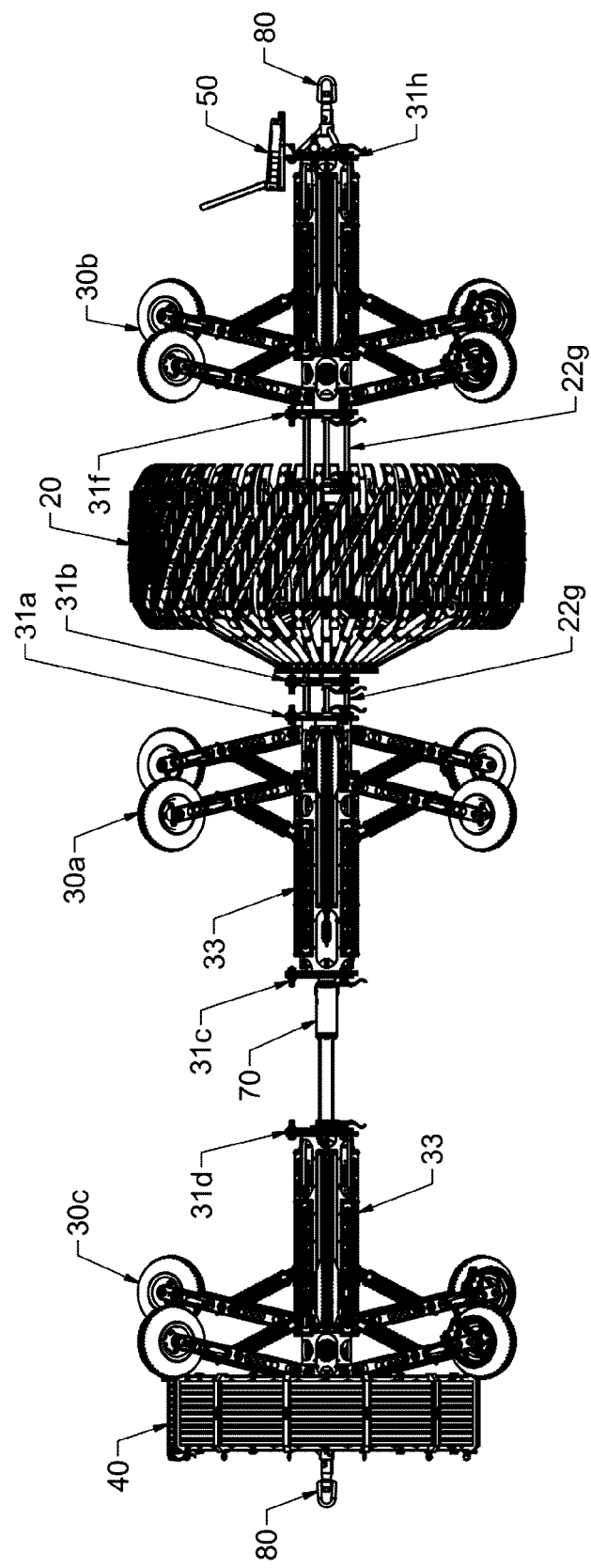
FIG. 9 is a front perspective view of the apparatus of FIG. 1, according to an embodiment of the present disclosure.
Figure 10:
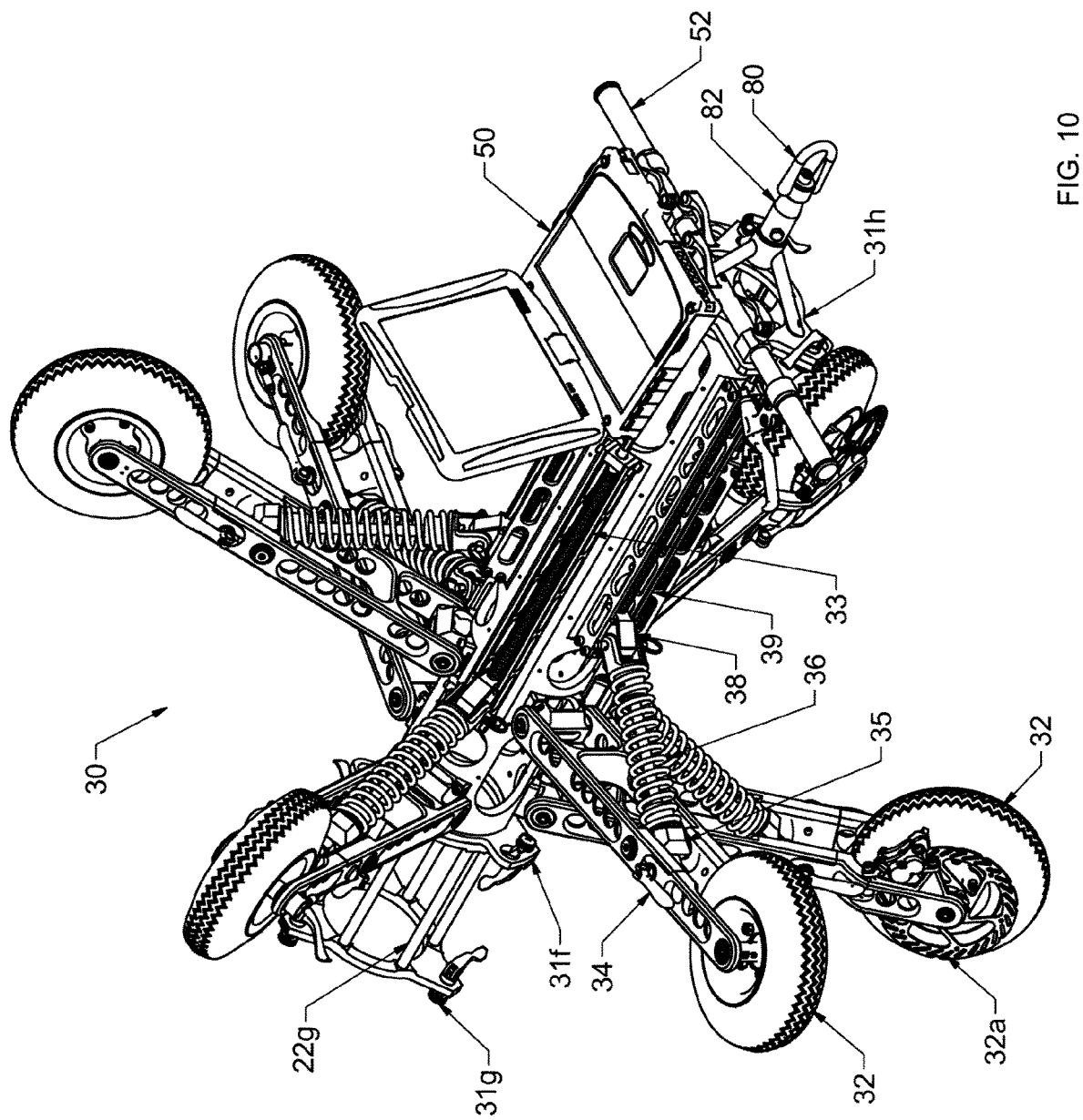
FIG. 10 is a partial perspective view of one set of the guide wheels of FIG. 1, according to an embodiment of the present disclosure.

The apparatus 10 may also include two or more guide wheel assemblies 30. As illustrated in the example of FIGS. 1 and 9, each end of the sensor assembly 20 is connected with a guide wheel assembly 30a or 30b. In the example of FIGS. 9 and 10, the rods 22g are securely connected to two flanges 31a and 31f. The guide wheel assembly 30a is secured to the flange 31a and the guide wheel assembly 30b is secured to the flange 31f. The guide wheel assemblies 30, including 30a, 30b, and 30c are constructed in substantially the same manner described below. As illustrated in the example of FIG. 10, each of the guide wheel assemblies 30a 30b and 30c includes a plurality of guide wheels 32, a plurality of support beams 33, a plurality of wheel arms 34, and a plurality of springs 36. As illustrated in the example of FIG. 9, a plurality of support beams 33 of guide wheel assembly 30a are installed between the flanges 31a and 31c, a plurality of support beams 33 of guide wheel assembly 30c are installed between the flanges 22f (FIG. 3) and 31d. A plurality of support beams 33 are installed between the respective flanges of the respective guide wheel assemblies. A first end of a wheel arm 34 is pivotally installed on the support beams 33. A guide wheel 32 is rotatably installed between a pair of wheel beams 34. For example, each end of an axis of a wheel 32 is rotatably installed at a wheel arm 34. Each of the support beams 33 is adapted to receive a pair of wheel arms 34 when the arms are retracted. Each pair of the wheel arms 34 has a spring 36 which may have a first end 35 installed above the wheel 32 and between a pair of wheel arms 34 and a second end 38 pivotally mounted to a channel 39. When the pair of wheel arms 34 retract, such as when the diameter of the pipe becomes smaller, the spring 36 is a compressed state. The spring 36 may slide along the channel 39, for example via a lead screw, to retract or expand wheel arm 34. When the diameter of the pipe becomes greater, decompression of the spring 36 pushes the wheel arms 34 away from the channel 39 and the pair of wheel arms 34 extends until the wheel 32 contacts with the inner wall of the pipe.

As such, due to the pivotal arrangement of the wheel arms 34 and the second end of the spring 36, and due to the nature of the spring and the ability of spring 36 to slide along the channel 39, the guide wheel assembly 30 may expand or retract when the diameter of the pipe varies, so that the guide wheels 32 of the guide wheel assembly 30 are always in contact with the inner wall of a pipeline when the apparatus 10 is in operation. The guide wheels 32 are rotatably movable along within the pipe, such as along the direction of the axis of the pipe. As such, the position of the guide wheel 32 may be adjusted to keep the wheel 32 in contact with the pipe wall even when the diameter of the pipeline changes. The maximum and minimum diameters of the pipeline in which the wheel assemble 30 may be used may be commensurate with the respective maximum and minimum diameters of the sensor assembly 20. In some examples, the wheel assembly 30 may extend to a greater extent and/or retract to a smaller extent than the sensor assembly 20. In this case, the maximum and minimum diameters of the pipe in which the apparatus 10 may be used are the maximum and minimum diameters supported by the sensor assembly 20.

Figure 13:
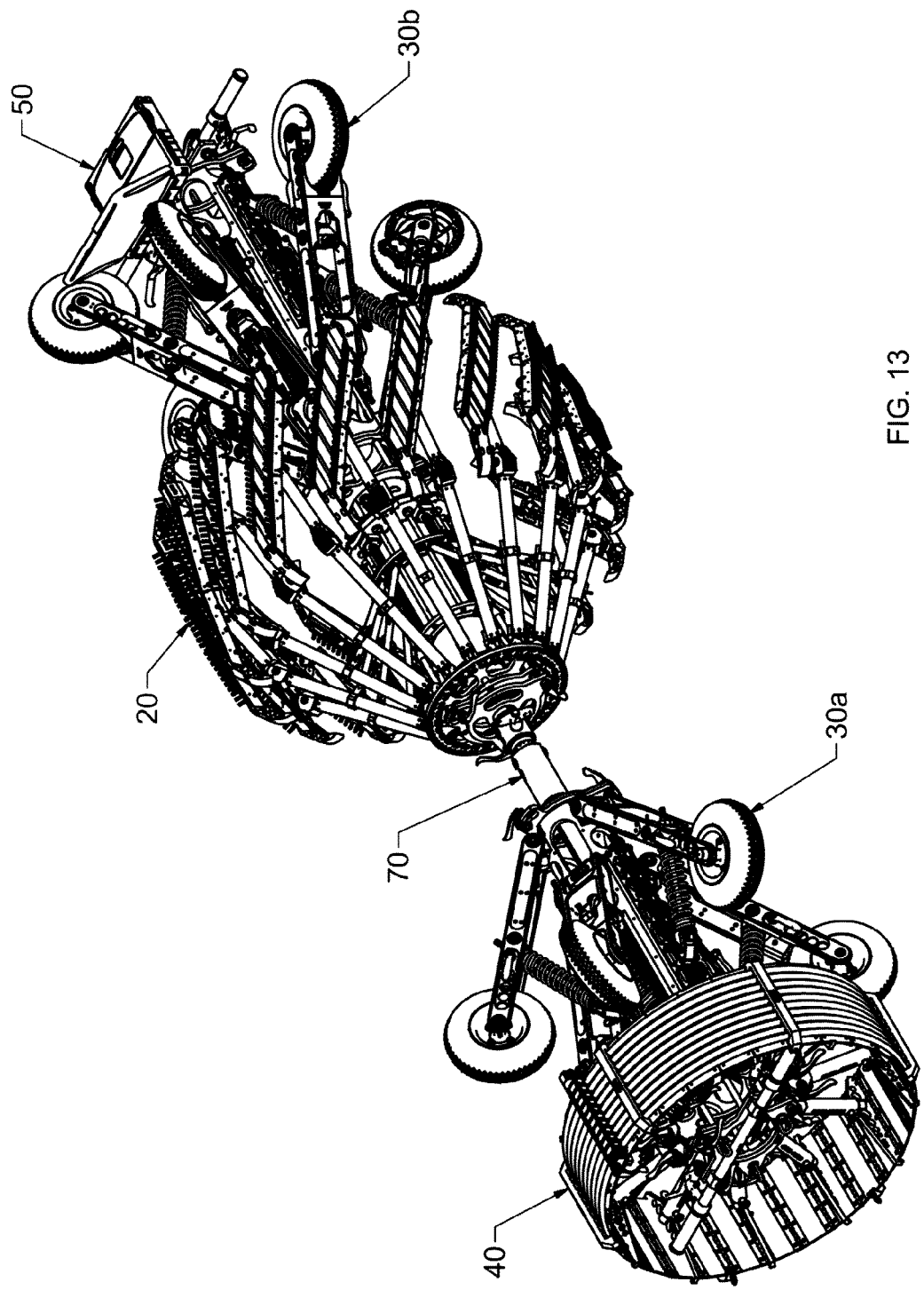
FIG. 13 is a perspective view of the apparatus, according to another embodiment of the present disclosure.
Figure 14:
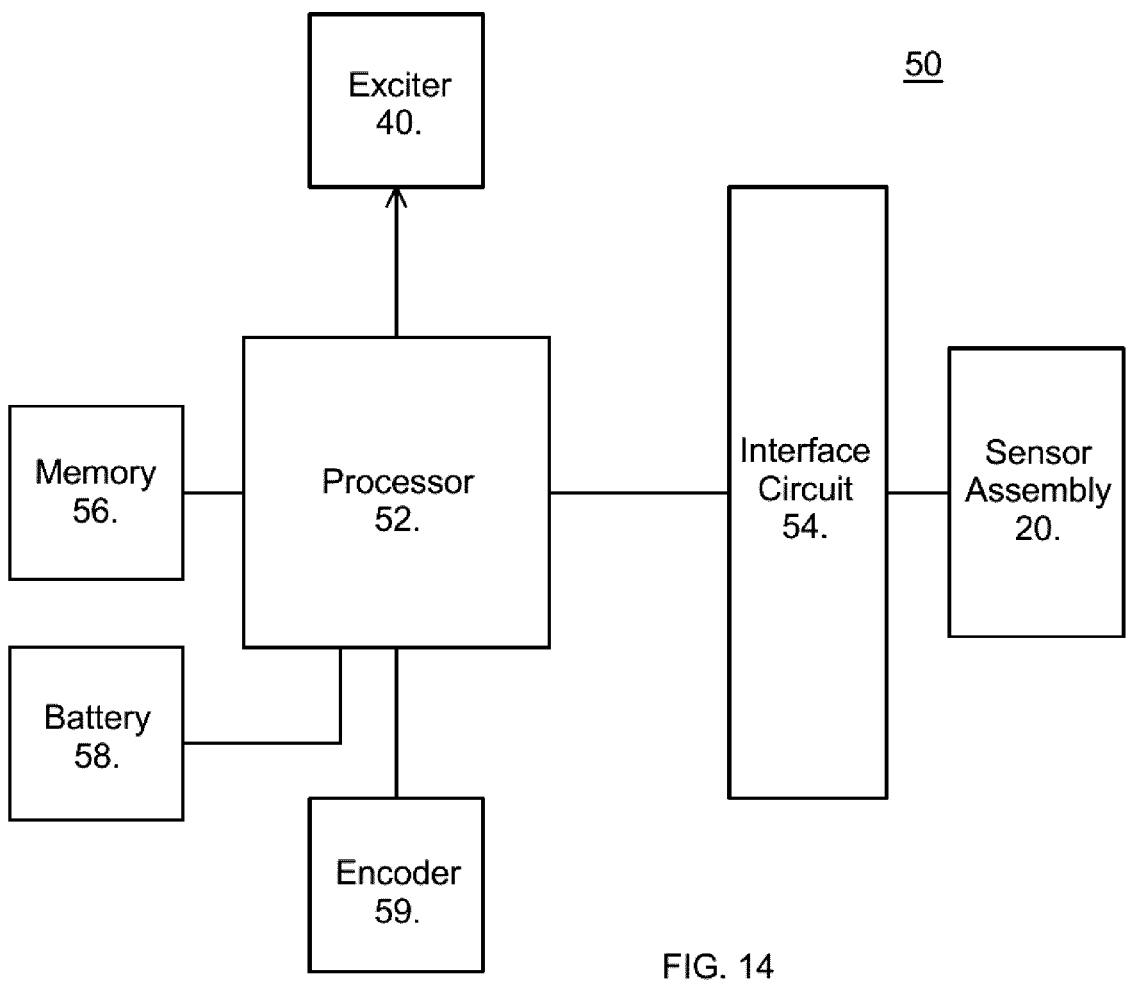
FIG. 14 is a block diagram of a control unit, according to an embodiment of the present disclosure.

In the example of FIG. 10, each wheel assembly 30 includes 6 wheels. The number and the position of the wheel assemblies 30 may be varied, as long as the apparatus 10 can move stably along the pipeline. In the example of FIG. 13, apparatus 10 may only need two sets of guide wheel assemblies 30a and 30b to stably move along the pipeline. The mounting position of the wheel assemblies 30 may be varied.

In some examples, each wheel 32 may include a brake 32a. When actuated, such as by a hand handle 52 (FIG. 10), the brake 32a prevents the wheel 32 from rotating and thus stops the movement of the apparatus 10.

In some examples, an operator may manually move the apparatus 10 through a pipe with a handle 52 or a winch, as illustrated in FIG. 10. In some examples, the apparatus 10 may be autonomously moved inside a pipe, such as by an engine controlled by the control unit 50, or by a robot. The movement of the guide wheel assembly 30 causes the movement of the apparatus 10 inside the pipeline and thus cause the sensor assembly 20 to sense the EM signals of the inner pipe wall along the length of the pipe.

Figure 11A:
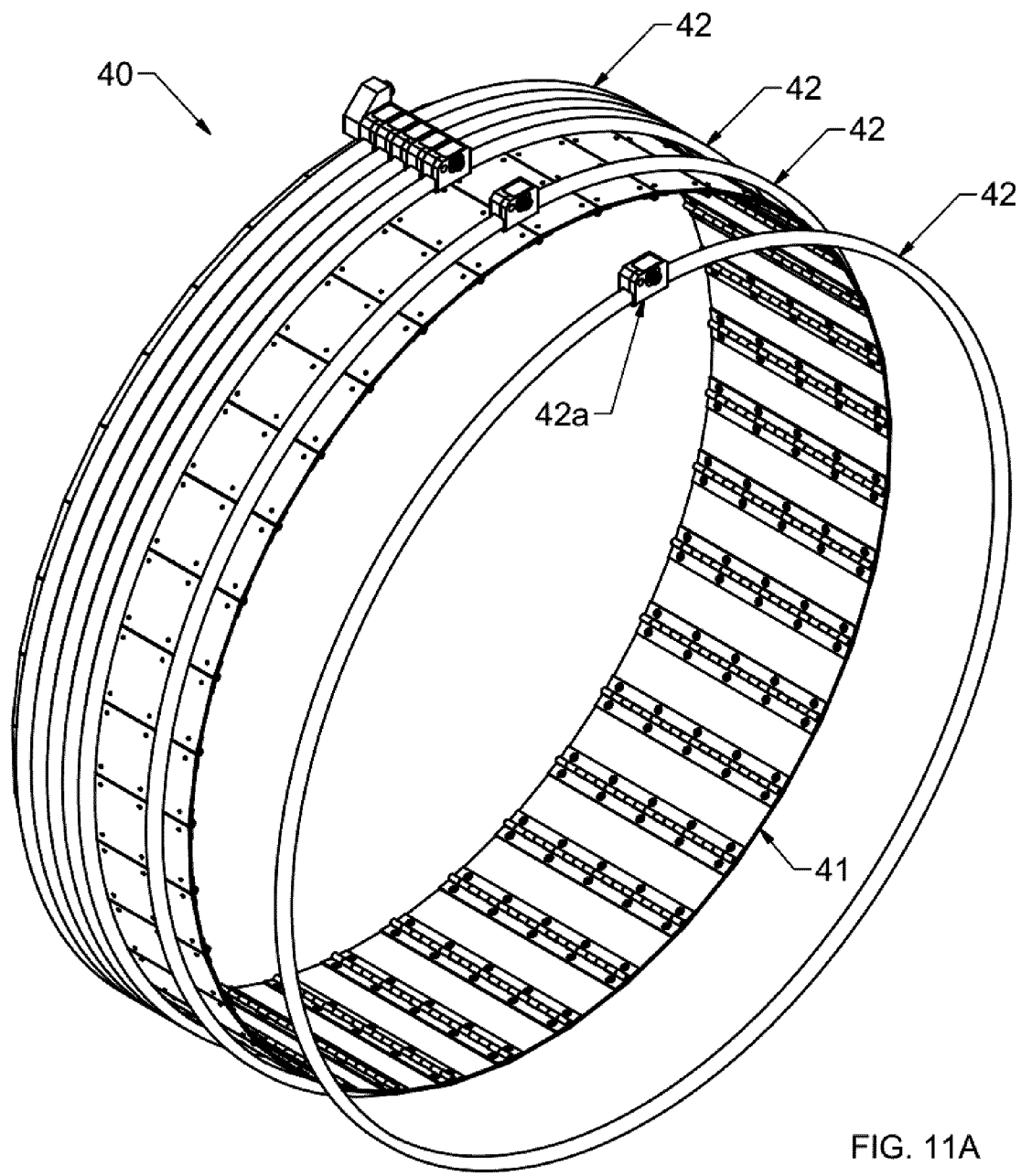
FIG. 11a is a partial perspective views of an exciter of the apparatus of FIG. 1, according to an embodiment of the present disclosure.
Figure 11B:
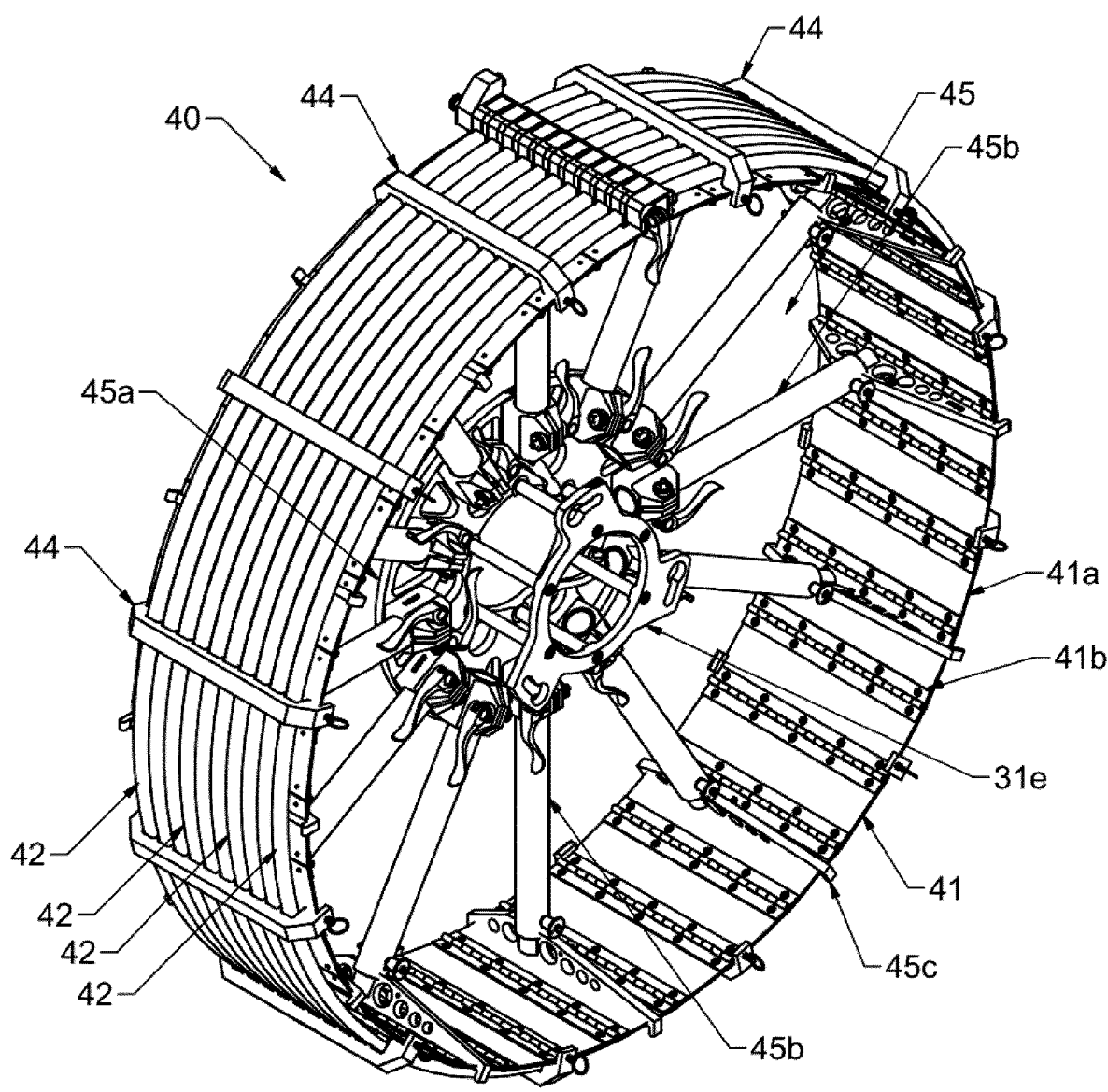
FIG. 11b is a perspective views of an exciter of the apparatus of FIG. 1, according to another embodiment of the present disclosure.

In some examples, the apparatus 10 may include one or more attachments 80, as illustrated in FIG. 9, such as tow ring attachments, mounted at the front end, and/or the rear end of apparatus 10. In the example of FIG. 1, the support frame 82 may be mounted on the flange 31e (FIG. 11B). In the example of FIG. 10, the support frame 82 may be mounted on the flange 31c.

The attachments provide a connecting point for pulling and winching the apparatus 10 by a person or a cart inside the pipe, including at up and down slopes inside the pipe.

The exciter 40 generates an electromagnetic (EM) field to induce electric currents or magnetic fields or EM fields inside the metal wall of a pipeline. In the example of FIGS. 11A and 11B, the exciter 40 includes a plurality of electrically interconnected coils 42 and a support structure 41. The coils 42 may be made from conductive materials, such as copper. The shape of the coils 42 may be substantially circular. As illustrated in FIG. 11A, the coils 42 are detachable from the support structure 41, and from each other, to allow easy access through a manway into the pipe. When a modulated current generated by the control unit 50 passes through the coils 42, the exciter 40 generates an electromagnetic field.

As illustrated in the example of FIG. 11A, the coils 42 may be mounted on the support structure 41. The support structure 41 may be made of ferromagnetic materials 41a, such as iron or steel or stainless steel plates. In some examples, the support structure 41 may be made of a plurality of interconnected SS440 magnetic stainless steel plates. A plurality of hinges may be used to connect the steel plates. Any two adjacent steel plates are connected by at least one hinge 41b. The interconnected steel plates form the support structure 41, such as a steel bracelet core. The support structure 41 may have an external diameter that allows the coils 42 may securely mounted on the external surface of the support structure 41. The coils 42 may be mounted on the external surface of the support structure 41 to form the exciter 40. As illustrated in FIG. 11A, each coil 42 has a connector 42a to detachably connect to the connector 42 of adjacent coils 42. The interconnected connectors 42 are also electrically connected. The modulated current may input from one of the connector 42a to the coils 42 to form AC current loop. The AC current loop in the coils 42 in turn generates EM field to excite the wall of the pipe.

Since the support structure 41 is made of ferromagnetic material 41a, the support structure 41 also amplifies the EM field generated from the coils 42. By linking the steel plates with hinges, the support structure 41 is collapsible, and the coils 42 may be detached from the support structure 41 and from each other by separating the connectors 42a of the coils 42. As such, the exciter 40 may fit through a manhole. The coils 42 and the support structure 41 may then be assembled in the manhole to form the exciter 40 for testing the pipe.

As illustrated in the example of FIG. 11B, the exciter 40 may include an internal structure 45 to support the support structure 41. In FIG. 11B, the internal structure 45 includes a hub 45a and a plurality of spokes 45b. Each spoke has one end securely connected to the hub 45a, and the other end contacted to the internal wall of the support structure 41 to maintain the substantially circular shape of the support structure 41. In some examples, the internal structure 45 further includes a plurality of side bars 45c, the other end of each spoke 45b is mounted to the side bar 45c, and each of the side bar 45c extends vertically against the internal wall of the support structure 41. In this case, the support of the internal structure 45 and the internal wall of the support structure 41 is enhanced, as the contacting area between side bar 45c and the internal wall of the support structure 41 is increased. The plurality of the spokes 45b may have the same length and may be evenly distributed on the hub 45a, namely that the angle formed by every two adjacent spokes have the same degree. In the Example of FIG. 11B, the exciter 40 may also include a flange 31e mounted on the hub 45a for support an attachment 80 to be discussed below.

As illustrated in the example of FIG. 11B, the exciter 40 may include one or more spacers 44 for retaining all the coils 42 onto the support structure 41. The spacers 44 may releasably attach to the outer surface of the coils 42 for protecting the coils 42 from direct contacting with the inner wall of a pipe. As such, the coils 42 may not be scratched or damaged by the wall of the pipe as the apparatus 10 advances within the pipe. The spacers 44 may be made from non-conductive materials, such as plastic.

The exciter 40 may be placed in front of the sensor assembly 20 in the movement direction of the apparatus 10. After the metal wall of the pipeline has been excited by the EM fields generated by the exciter 40, the sensors 23*d* of the sensor assembly 20 may measure the residue EM fields of the metal wall of the pipe. The EM fields received from the sensors 23*d* may be from the remote EM field coupling generated by the exciter 40 through the pipe wall in real time.

The exciter 40 has a diameter that can fit into the pipe to be tested. In some examples, the exciter 40 has a diameter as large as possible to fit through the range of pipe diameters. Generally, exciter 40 with a larger diameter induces stronger electric currents or magnetic fields or both on the metal pipe wall, and thus the sensors 23*d* sense stronger signals and produces better quality of data.

In the example of FIGS. 1 and 9, the apparatus 10 may include a flex joint 70. As illustrated in greater detail in FIGS. 12A and 12B, the flex joint 70 may be mounted between the exciter 40 and the sensor assembly 20. The flex joint 70 may include a shaft 71, a flex joint body 72, and a locking mechanism 73.

Figure 12A:
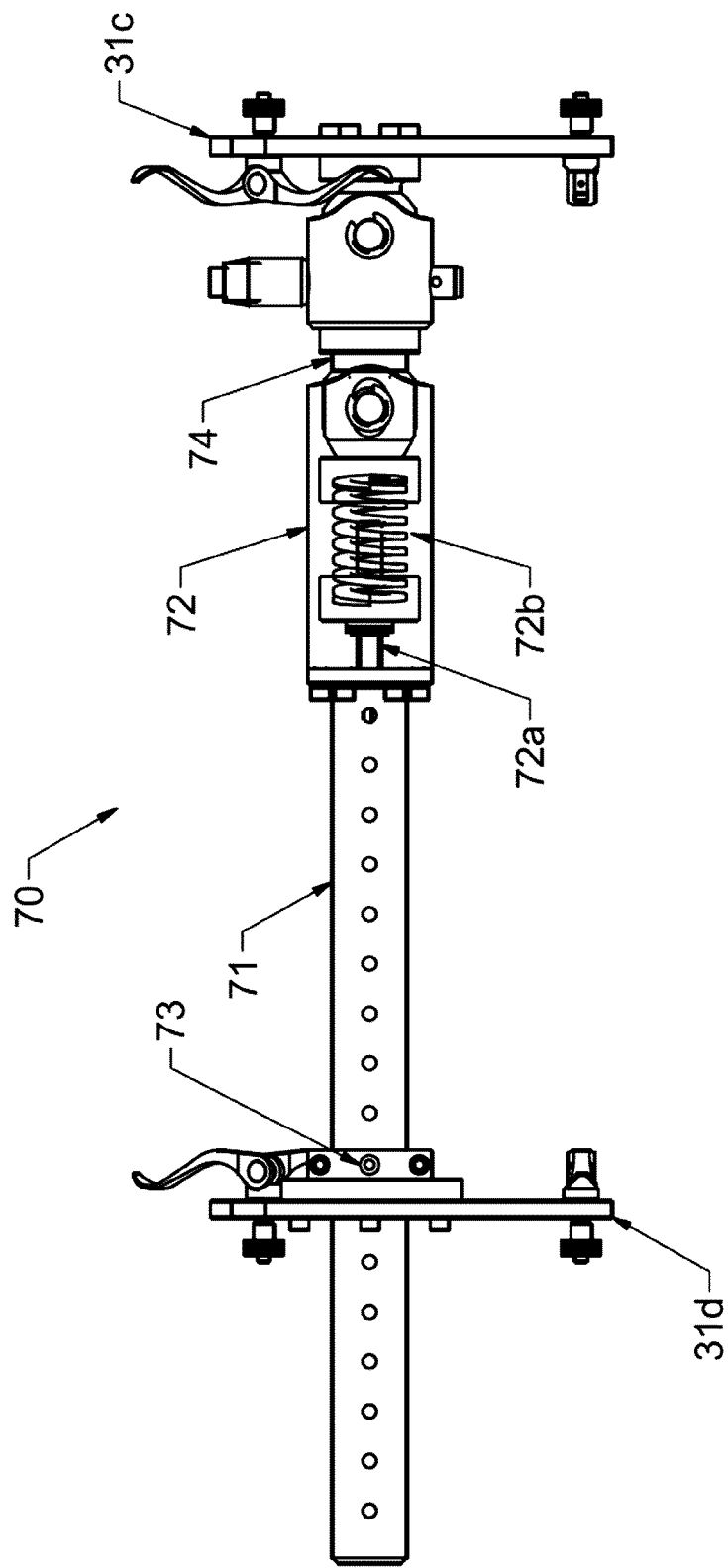
FIG. 12A is a front view of a flex joint mounted on the apparatus of FIG. 1, in a straight configuration.
Figure 12B:
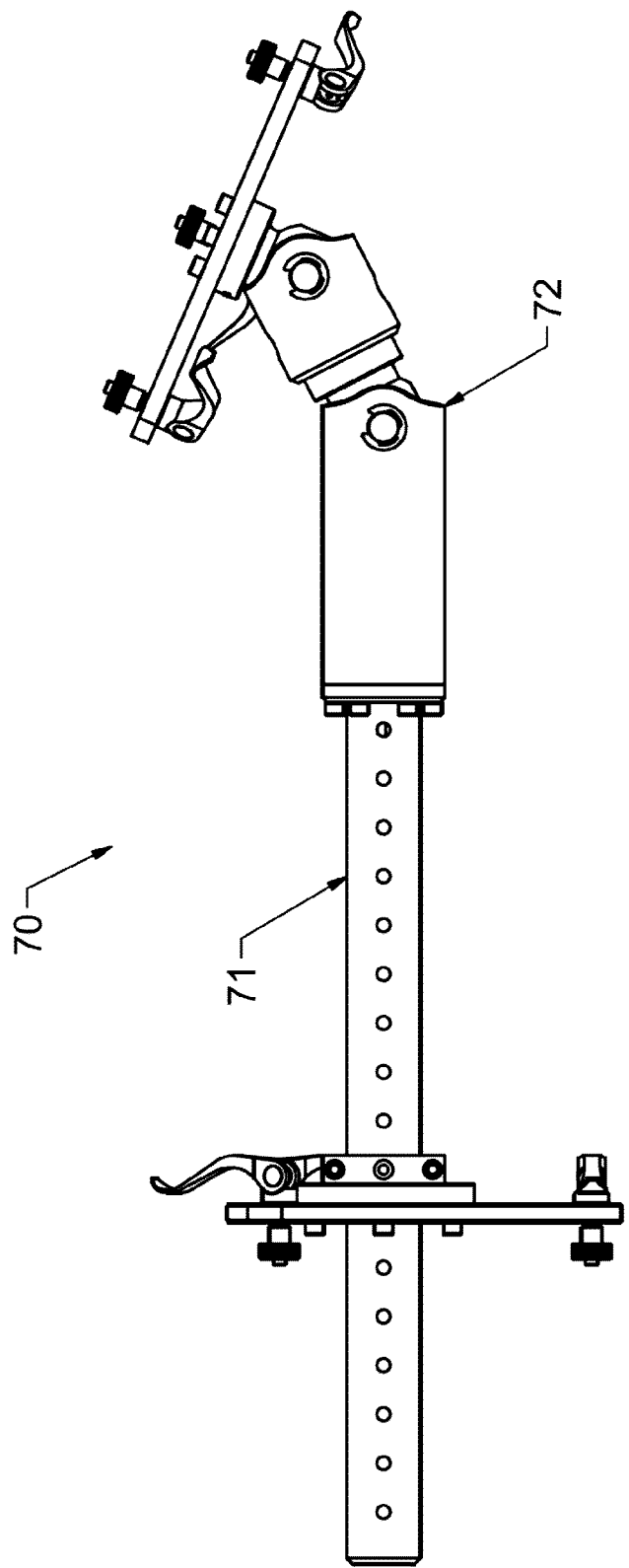
FIG. 12B is a front view of a flex joint mounted on the apparatus of FIG. 1, in a bent configuration.

The shaft 71 has one end mounted on the flange 31*d* and the second end secured mounted on the flex joint body 72. The shaft 71 allows a person operating the apparatus 10 to adjust the overall length of the flex joint by changing the distance between the exciter 40 and the sensor assembly 20 in order to optimize the sensitivity of the apparatus 10 for various pipe sizes. The distance between the exciter 40 and the sensor assembly 20 may be adjusted by intruding a desired length of the shaft 71 into central space defined between the flanges 31*d* and 31*e* (FIG. 11B). After the distance of intrusion of the shaft 71 has been determined, the locking mechanism 73 may then lock the shaft at the desired position to provide the desired distance between the exciter 40 and the sensor assembly 20. In the example of FIGS. 12A and 12B, the body of the shaft 71 may include a plurality of bores and the locking mechanism 73 has at least one groove for releasably engaging at least one bores on the body of the shaft 71, so that the shaft 71 is secured at the desired position. When the position of the shaft 71 needs to be adjusted, the groove may be pull away to disengage the bore, and the position of the shaft 71 may be further adjusted, and the groove may reengage the bore for locking the shaft 71 in the new position. In some examples, the flange 31*d* may be locked into the shaft 71 with a screw.

In the example illustrated in FIG. 12A, the flex joint body 72 may have a center screw 72*a* to adjust a nut which compresses a spring 72*b* which pushes a plunger against a ball joint. This mechanism allows to loosen the joint 74 to bend the apparatus 10, as illustrated in FIG. 12B. As such, the overall bent apparatus 10 may traverse and scan tight bend sections of a pipe. This mechanism also allows to tighten up and stiffen the apparatus 10, as illustrated in FIG. 12A, for scanning straight sections of a pipe.

The joint 74 may be adjusted from the exciter 40 side of the apparatus 10 via the extendable shaft 71 to dock with the center screw 72*a* so that it can be reached by the person operating the apparatus 10.

Dimensions of the apparatus 10 may be varied. For example, dimensions of apparatus 10 may be reduced if the pipe to be scanned has a smaller diameter. FIG. 13 illustrates another embodiment of apparatus 10, in which the diameter of the exciter 40 and the diameters of the sensor assembly 40 in the extended state are reduced to fit into the pipe to be scanned. As well, the configuration of the apparatus 10 may be varied. The apparatus 10 may use universal coupling interfaces, such as joints or coupling, for interconnecting its components or modules. In the example of FIG. 13, the overall dimension of the apparatus 10 has been reduced, the apparatus 10 has a reduced weight, and the apparatus 10 only needs two sets of guide wheel assemblies 30*a* and 30*b* to keep the apparatus stable in testing. In some examples, one or more additional set of guide wheel assemblies may be added.

As illustrated in FIG. 10, the control unit 50, for example a computer, may include an interface circuit 54, a memory 56, and a processor 52. The interface circuit 54 receives the sensed signals or data from the metal wall of a pipe from the sensors 23*d* of the sensor assembly 20. The control unit 50 may store the measured signals or data in the memory 56 for processing. The processor 52 controls the interface circuit 54 to receive the measured signals and controls the memory 56 to store the signals saved to the memory 56. In some examples, the processor 52 also records data from an encoder 59 measuring axial displacement along the pipe. The encoder 59 may be located on one of the guide wheels 32, or on a separate encoding wheel placed on the apparatus 10, such as on the body of the apparatus 10 in between the guide wheel assemblies 30*c* and 30*a*. The encoder 59 electrically connected with the processor 52, for example, by data bus. The encoder 59 may record the distance information along with the EM data so that the sensed EM field data, including the data indicating defects of the pipe, may be correlated to a specific location along the pipe length. The processor 52 may also process the sensed signals or data and determine the defects of the pipe. The sensed EM data reveals the amount of material of the pipe wall near each sensor 23*d*. If less material is present at a point of the pipe wall than expected, then the point of the wall are likely corroded. In some examples, the sensed data in the memory 56 may be exported to an external computer outside the pipe for further analysis at a later time. In some examples, the sensed data in the memory 56 are processed by the processor 52 in real time. The processor 52 may be a central processing unit (CPU) and the memory may be a random-access memory (RAM), flash memory (used as secondary memory) and ROM, PROM, EPROM and EEPROM memory, dynamic random-access memory (DRAM), and fast CPU cache memory, such as static random-access memory (SRAM).

With the angled arrangements of the sensor bars 23 and the sensors 23*d*, the sensor assembly 20 may output sensed signals or data that may overlap over a point of the pipe wall. The sensors 23*d* that overlap may produce identical or very similar signals or data. The control unit 50 is capable of identifying whether these signals or data are generated by sensors 23*d* from an overlapped point of the pipe wall. The signals or data are generated by sensors 23*d* from an overlapped point may be ignored or discarded by the processor.

Figure 15:
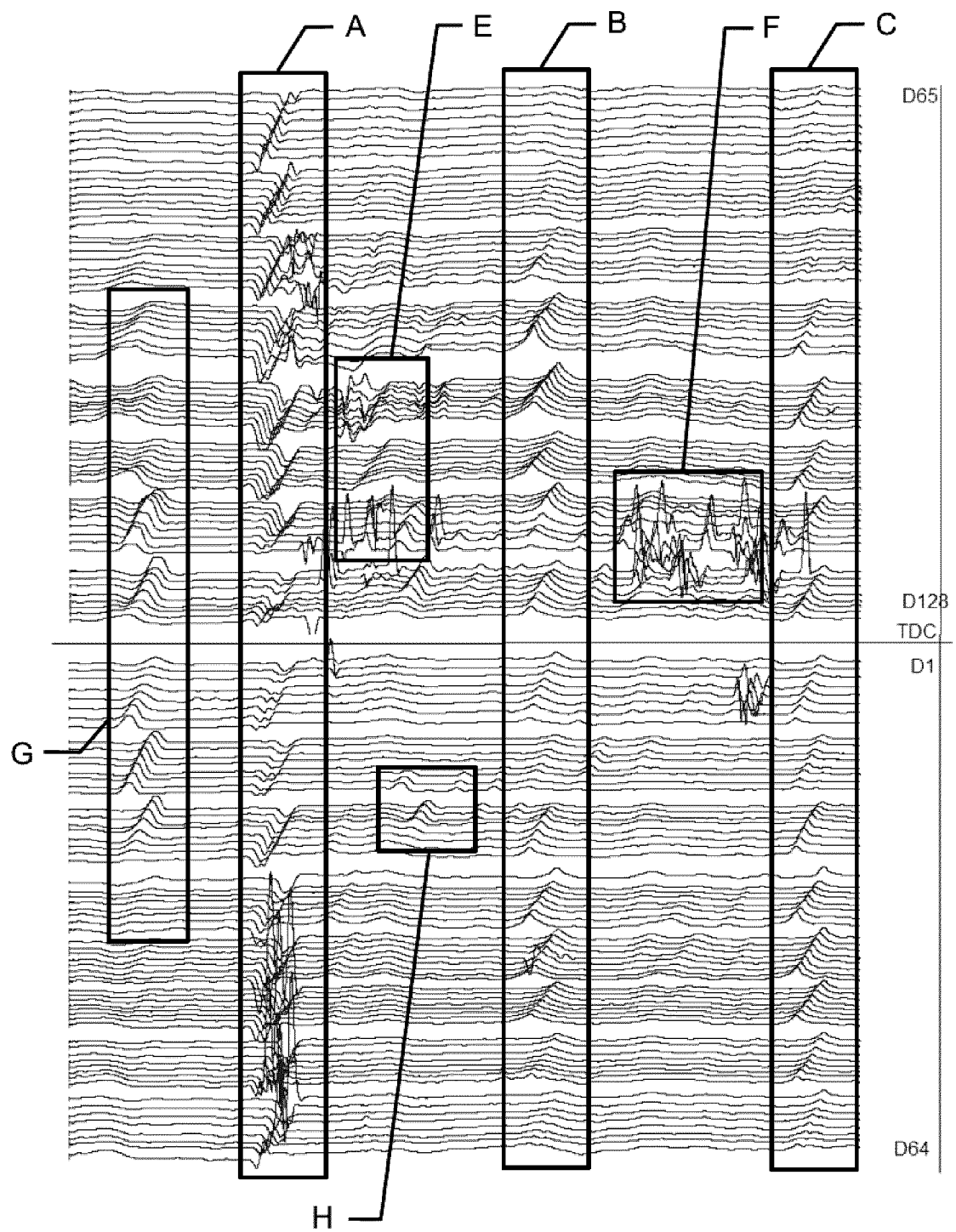
FIG. 15 is a diagram illustrating the sensed data traces by using the apparatus in FIG. 1.

The defects are identified using the pattern of appearance, and phase and amplitude behavior of the sensed signals. FIG. 15 is an example of determining the defect based on the amplitude behavior of the sensed data. In the example of FIG. 15, each trace is the output of data or sensed data from a single sensor 23*d* over a period of time. The sensed data are arranged into groups of a plurality sensors 23*d*, such as eight sensors, with distance travelled shown from left to right. In the example of FIG. 15, the sensed data of 16 sensor bars 23 are illustrated, and each sensor bar 23 includes 8 sensors 23*d*. In FIG. 15, a disturbance in substantially all of the traces at substantially the same positions in each of three places A, B and C are caused by pipe joints. The disturbances in substantially all of the traces at, for example E, F, are caused by sensor movement or vibration at the corresponding points of the inner wall of the pipe. The disturbances in only some of the traces measured by a sensor bar 23, for example at G and H in FIG. 15, are caused by damage in the pipe wall. The traces indicating defects typically have modest amplitude changes which are distributed in isolated areas of the entire trace distribution of one or more sensors 23*d* or sensor bars 23, as shown in the example of G and H. The traces indicating defects are generally not distributed in all of the sensor bars 23 or are not with significant amplitude changes as shown in E and F.

In some examples, the control unit 50 may include a battery 58 for supplying a current to the processor 52, and the processor 52 modulates the current and supplies the modulated current to the coils 42 of the exciter 40 to generate EM field.

The control unit 50 may be placed at any point of the apparatus 10. In the example of FIG. 1, the control unit 50 is placed at the end of the wheel assembly 30*b*.

In some examples, to reduce weight, the apparatus 10 may use lightweight materials. For example, each arm 23 may use lightweight materials, such as graphite composites.

The apparatus 10 may be used in pipes with various diameters, such as a diameter ranging from 36 inches to 60 inches. The apparatus 10 may also be used in pipes with both larger and smaller diameters.

Certain adaptations and modifications of the embodiments described above can be made. Therefore, the embodiments discussed above are considered to be illustrative and not restrictive.

The invention claimed is:

1. An apparatus for testing within a metal pipe, comprising:
   an exciter for generating an electromagnetic (EM) field for exciting a wall of the metal pipe;
   an extendable and retractable sensor assembly comprising a plurality of sensor bars for sensing residue EM field on the wall of the pipe, each sensor bar comprising a plurality of sensors, and having a first axis arranged in an angled manner with respect to a second axis of the pipe,
   the sensors in each sensor bar being arranged in such a manner that an axis of a sensor forms an angle with respect to the first axis of the sensor bar, the angle being in a range from about 20° to 70°;
   a plurality of guide wheel assemblies for supporting and moving the apparatus along the second axis of the pipe; and
   a control unit for processing the sensed residue EM field from the sensor assembly.

2. The apparatus of claim 1, wherein each of the sensors comprises coils.

3. The apparatus of claim 1, wherein the sensor assembly includes a plurality of expandable and retractable arms, and each arm has a sensor bar.

4. The apparatus of claim 3, wherein the each arm is made of graphite composites.

5. The apparatus of claim 1, wherein the sensor bars are substantially parallel to a surface of the wall of the pipe when the apparatus advances along the pipe.

6. The apparatus of claim 1, wherein the sensor bars are configured to be in contact with the wall of the pipe when a diameter of the pipe changes.

7. The apparatus of claim 1, wherein the sensor bars include bristles.

8. The apparatus of claim 1, wherein the guide wheel assemblies are extendable and retractable.

9. The apparatus of claim 1, wherein each of the guide wheel assemblies includes a brake.

10. The apparatus of claim 1, further comprising a handle for manually moving the apparatus through the pipe.

11. The apparatus of claim 1, wherein the control unit includes a battery for supplying a current to a processor, and wherein the processor modulates the current and supplies the modulated current to the exciter to generate the EM field.

12. The apparatus of claim 1, wherein the exciter comprises a plurality of conductive coils.

13. The apparatus of claim 12, wherein exciter further comprises a support structure and the plurality of conductive coils are mounted on an external surface of the support structure.

14. The apparatus of claim 13, wherein the support structure is collapsible to fit through a manhole.

15. The apparatus of claim 12, wherein the plurality of conductive coils are detachable from each other.

16. The apparatus of claim 12, wherein each of the plurality of conductive coils has a connector for receiving current input.

17. The apparatus of claim 12, wherein the exciter comprises at least one spacer for binding the plurality of conducive coils on an external surface of a support structure.

18. The apparatus of claim 1, further comprising an attachment mounted at a front end and/or a rear end of the apparatus.

19. The apparatus of claim 18, wherein the attachment is a tow ring attachment.

20. The apparatus of claim 1, further comprising a flex joint mounted between the exciter and the sensor assembly.

21. The apparatus of claim 1, wherein the apparatus comprises a first guide wheel assembly mounted at a first end of the sensor assembly, and a second guide wheel assembly mounted at a second end of the sensor assembly.

22. The apparatus of claim 21, wherein the apparatus comprises a third guide wheel assembly mounted between the exciter and the second guide wheel assembly.

23. A method for testing a metal pipe, comprising:
   generating an electromagnetic (EM) field;
   exciting a wall of the metal pipe with the EM field;
   providing an extendable and retractable sensor assembly comprising a plurality of sensor bars for sensing the EM field on a wall of a pipe, each sensor bar comprising a plurality of sensors, and having a first axis arranged in an angled manner with a second axis of the metal pipe the sensors in each sensor bar being arranged in such a manner that an axis of a sensor forms an angle with respect to the first axis of the sensor bar, the angle being in a range from about 20° to 70°;
   moving the sensor assembly along the second axis of the pipe; and
   sensing, by the sensor assembly, residue EM field on the wall of the pipe.

24. The method of claim 23, further comprising:
   outputting sensed data to a control unit; and
   detecting defects on the metal pipe.

25. An apparatus for testing within a metal pipe, comprising:
   an exciter for generating an electromagnetic (EM) field for exciting a wall of the metal pipe;
   a sensor assembly comprising a plurality of sensor supports for sensing residue EM field on the wall of the pipe, each sensor support having a first longitudinal axis, each sensor support including a plurality of sensors, each sensor having a second longitudinal axis that intersects the first longitudinal axis at an angle from 20° to 70°;

a plurality of guide wheel assemblies for supporting and moving the apparatus along the pipe; and a control unit for processing the sensed residue EM field from the sensor assembly.

26. The apparatus of claim 25, wherein the sensor assembly includes a plurality of expandable and retractable arms, each arm having one of the plurality of sensor supports mounted thereon.

27. The apparatus of claim 25, wherein the sensor supports are substantially parallel to a surface of the wall of the pipe.

28. The apparatus of claim 25, wherein the sensor supports are configured to be in contact with the wall of the pipe when a diameter of the pipe changes.

29. The apparatus of claim 25, wherein the sensors include coils.

* * * * *